(12) United States Patent
Brelivet

(10) Patent No.: US 9,045,723 B2
(45) Date of Patent: Jun. 2, 2015

(54) DEVICE AND METHOD FOR DISPENSING A PRODUCT INTO A PETRI DISH

(75) Inventor: Nicolas Brelivet, Saint Jouan de l'Isle (FR)

(73) Assignee: AES CHEMUNEX, Combourg (FR)

( * ) Notice: Subject to any disclaimer, the term of this patent is extended or adjusted under 35 U.S.C. 154(b) by 787 days.

(21) Appl. No.: 13/388,202

(22) PCT Filed: Jul. 30, 2010

(86) PCT No.: PCT/EP2010/061104
§ 371 (c)(1),
(2), (4) Date: Jan. 31, 2012

(87) PCT Pub. No.: WO2011/015528
PCT Pub. Date: Feb. 10, 2011

(65) Prior Publication Data
US 2012/0125483 A1 May 24, 2012

(30) Foreign Application Priority Data

Aug. 7, 2009 (FR) ...................................... 09 55568

(51) Int. Cl.
*B67C 3/00* (2006.01)
*C12M 1/26* (2006.01)
*C12M 1/22* (2006.01)
*C12M 1/00* (2006.01)
*B65B 43/60* (2006.01)

(52) U.S. Cl.
CPC ................ *C12M 33/04* (2013.01); *B65B 43/60* (2013.01); *C12M 23/10* (2013.01); *C12M 23/38* (2013.01); *C12M 23/50* (2013.01)

(58) Field of Classification Search
CPC .......... C12M 1/14; C12M 1/22; C12M 23/50; B65B 43/42; B65B 43/44; B65B 43/46; B65B 43/54; B65B 43/59; B65B 43/60
USPC ............. 141/1, 130, 165, 168, 172, 173, 174, 141/284, 369; 248/349.1; 53/250, 253, 281, 53/381, 468, 471, 109, 485
See application file for complete search history.

(56) References Cited

U.S. PATENT DOCUMENTS

| 2,853,210 A | 9/1958 | Stewart et al. |
| 2,987,163 A | 6/1961 | Eddison et al. |
| 3,704,568 A | 12/1972 | Duhring et al. |

(Continued)

FOREIGN PATENT DOCUMENTS

| DE | 197 50 912 A1 | 5/1999 |
| DE | 10339083 A1 | 3/2005 |

(Continued)

*Primary Examiner* — Jason K Niesz
(74) *Attorney, Agent, or Firm* — Harness, Dickey & Pierce, P.L.C.

(57) ABSTRACT

The disclosure relates to a device for dispensing a prescribed material into a Petri dish, each Petri dish including a removable lid capable of being arranged on a bottom that is not as broad as the latter, bringing the Petri dish to a material-dispensing station. According to the disclosure, the device includes a piston comprising a plate for supporting the bottom at the material-dispensing station and a device for rotating the plate on itself relative to the dispensing head, arranged so as to rotate the bottom relative to dispensing head in the position for dispensing the material into the bottom, in which the material outlet tip is arranged relative to plate in order to dispense the material into the rotated bottom.

12 Claims, 18 Drawing Sheets

(56) References Cited

U.S. PATENT DOCUMENTS

| | | |
|---|---|---|
| 3,704,768 A | 12/1972 | Hirozawa et al. |
| 3,844,896 A * | 10/1974 | Sharpe .................. 435/286.4 |
| 4,170,861 A | 10/1979 | Snyder et al. |
| 4,350,186 A | 9/1982 | Schalkowsky et al. |
| 4,468,914 A | 9/1984 | Pestes |
| 4,783,321 A | 11/1988 | Spence |
| 4,844,297 A | 7/1989 | Smith |
| 5,020,297 A * | 6/1991 | Borie et al. .................. 53/127 |
| 5,698,260 A | 12/1997 | Roth et al. |
| 5,787,687 A | 8/1998 | Mueller et al. |
| 6,199,605 B1 | 3/2001 | Inaba et al. |
| 6,302,302 B1 | 10/2001 | Albisetti |
| 6,303,389 B1 | 10/2001 | Levin et al. |
| 6,560,946 B2 | 5/2003 | Orange et al. |
| 7,105,338 B1 | 9/2006 | Holmes et al. |
| 7,306,768 B2 | 12/2007 | Chiga |
| 2011/0243814 A1 | 10/2011 | Brelivet |

FOREIGN PATENT DOCUMENTS

| | | |
|---|---|---|
| EP | 1 707 939 A1 | 10/2006 |
| FR | 2 579 749 A1 | 10/1986 |
| FR | 2 789 693 A1 | 8/2000 |
| FR | 2 789 694 A1 | 8/2000 |
| GB | 886795 A | 1/1962 |
| JP | 30-49676 A | 3/1991 |
| JP | 2003-225083 A | 8/2003 |
| WO | WO-2007/113561 A1 | 10/2007 |
| WO | WO-2008/003689 A1 | 1/2008 |
| WO | WO-2008/003696 A1 | 1/2008 |

\* cited by examiner

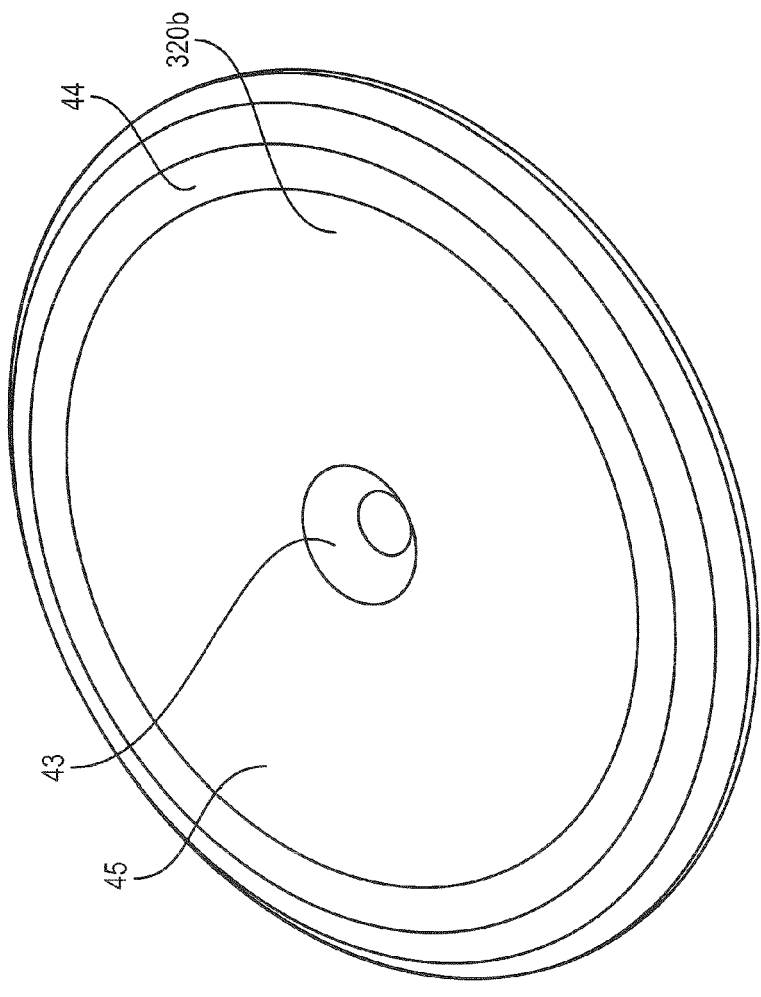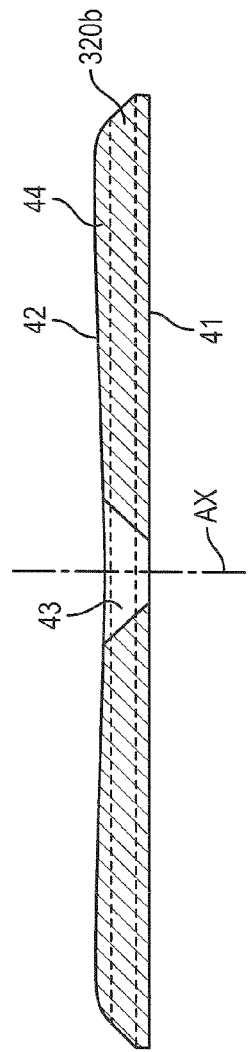
FIG. 2A
FIG. 2B

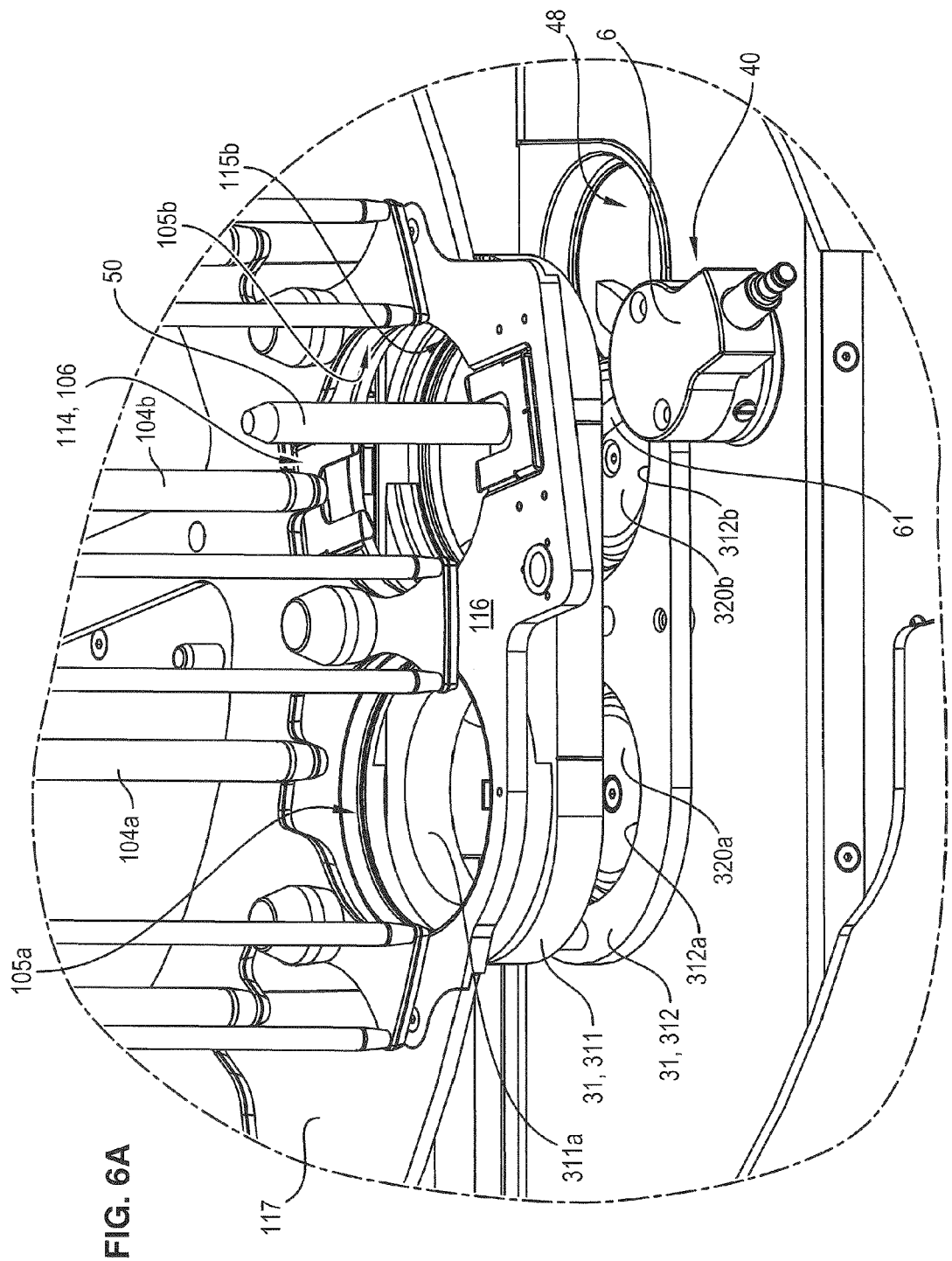

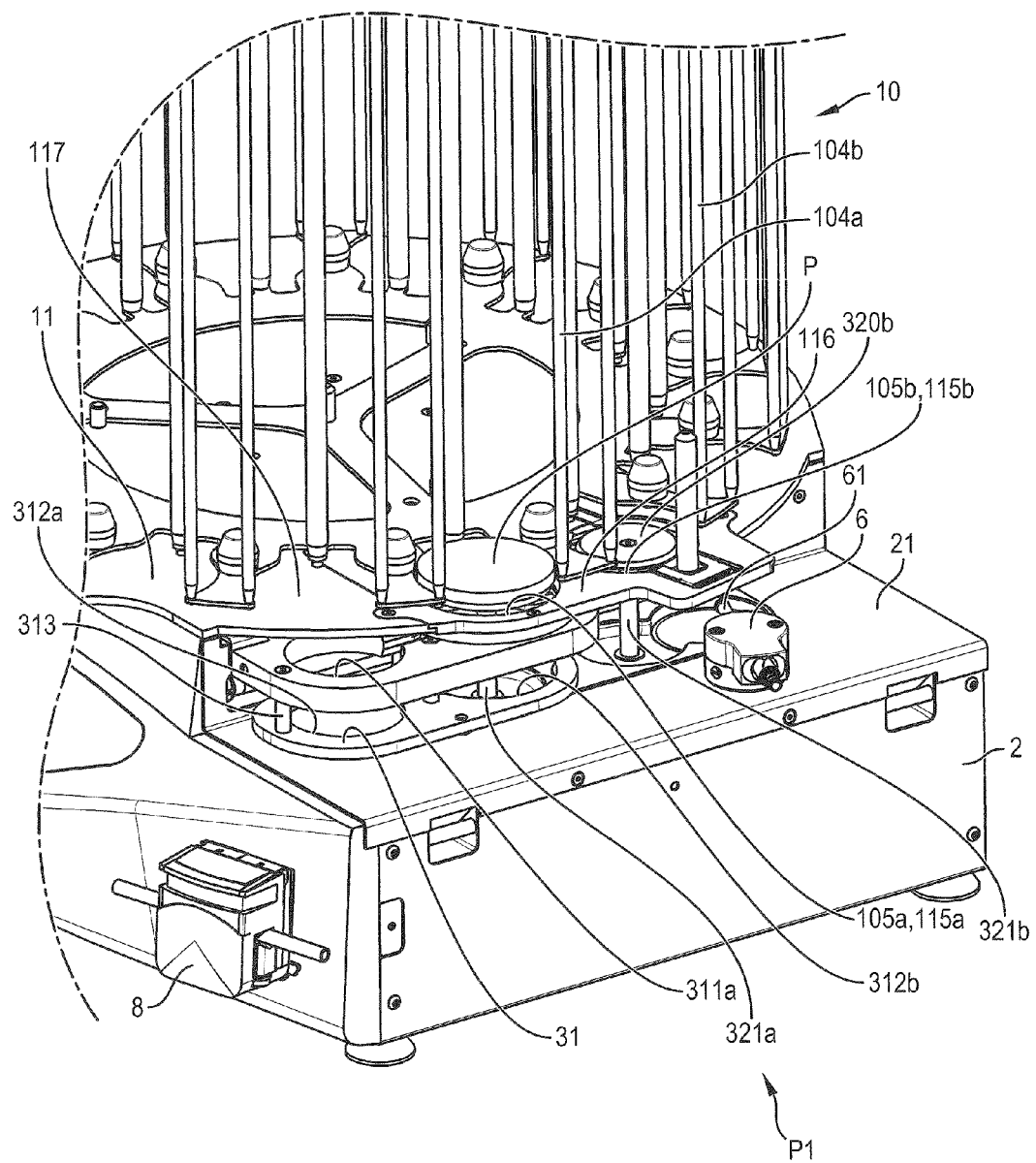

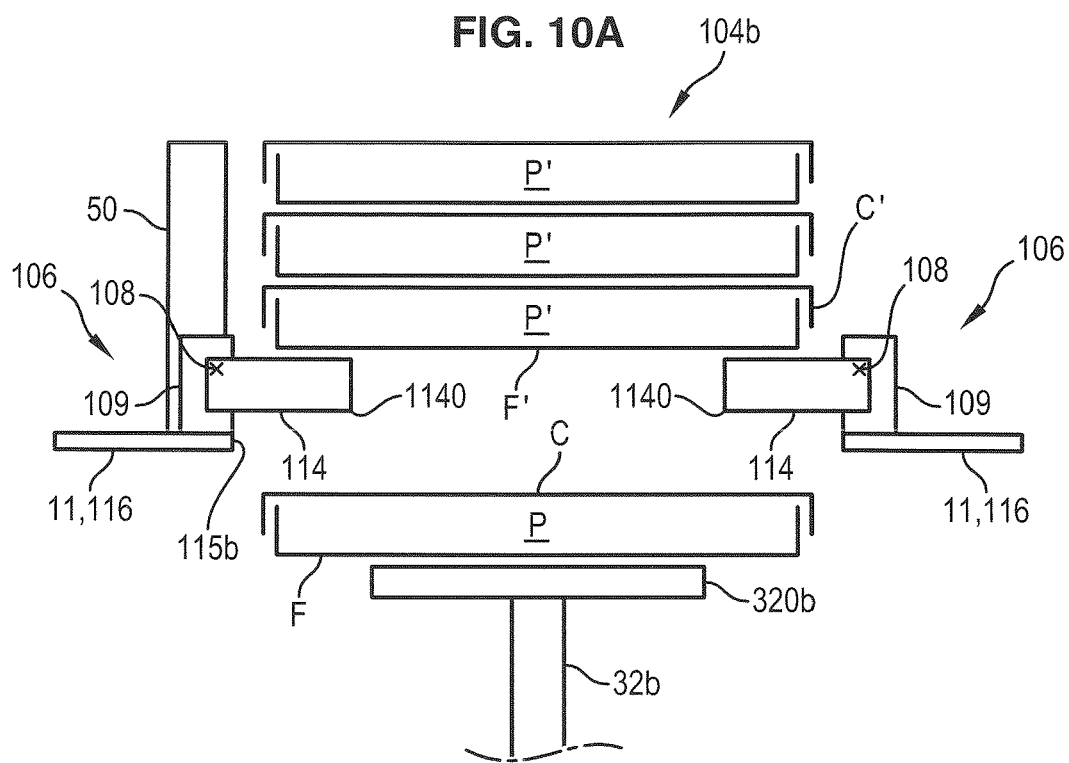
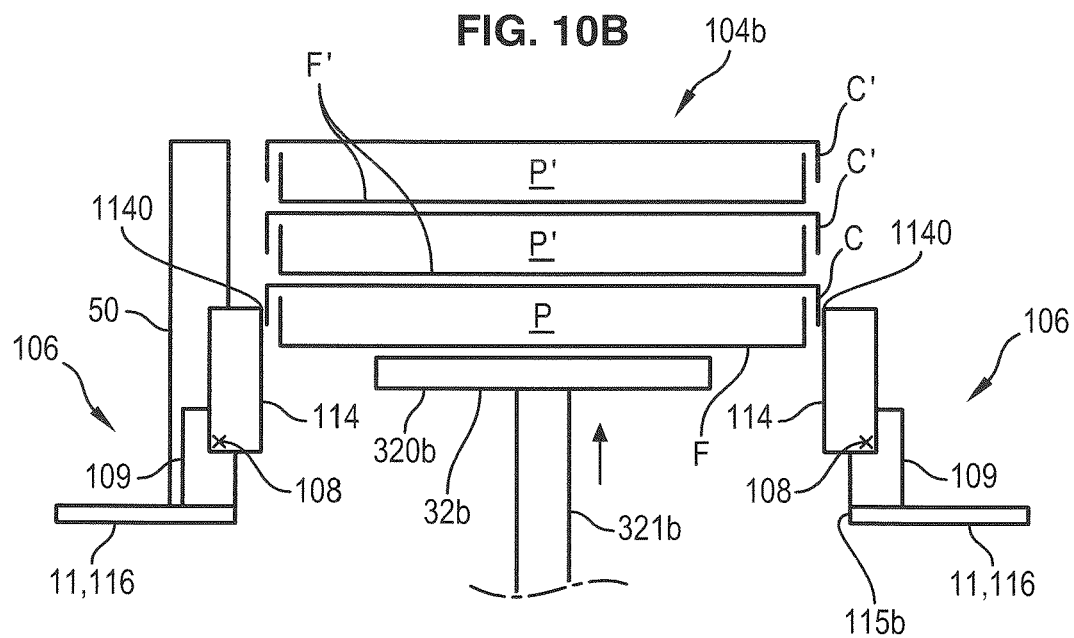

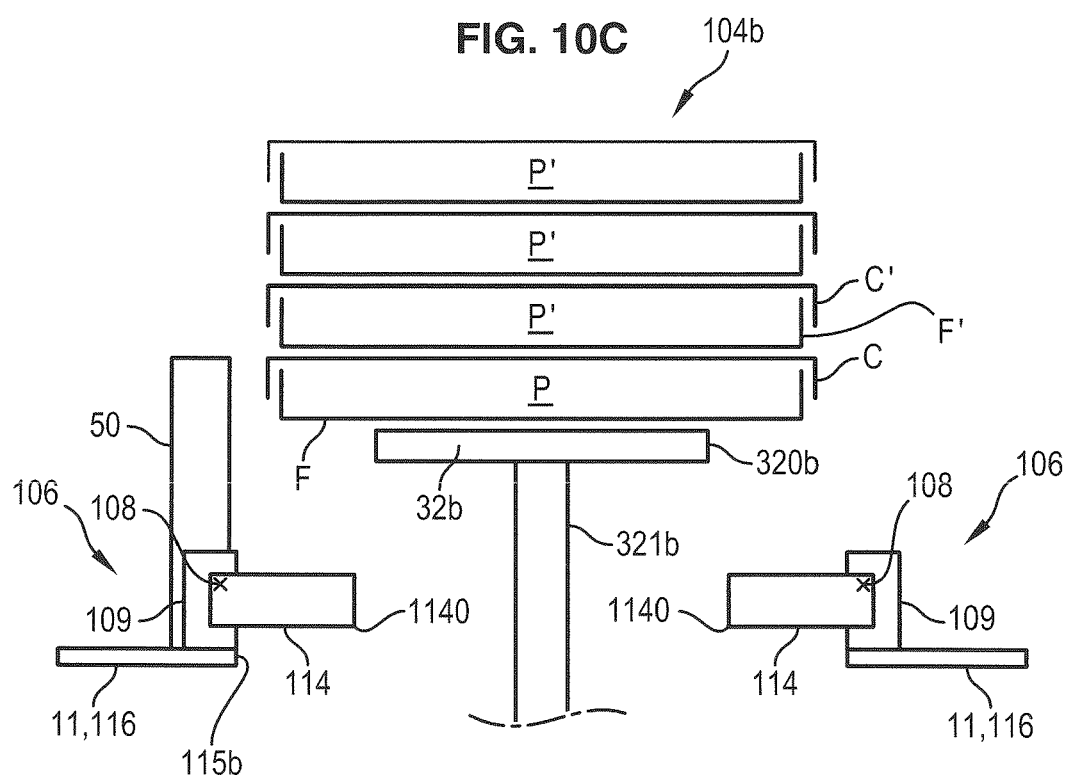
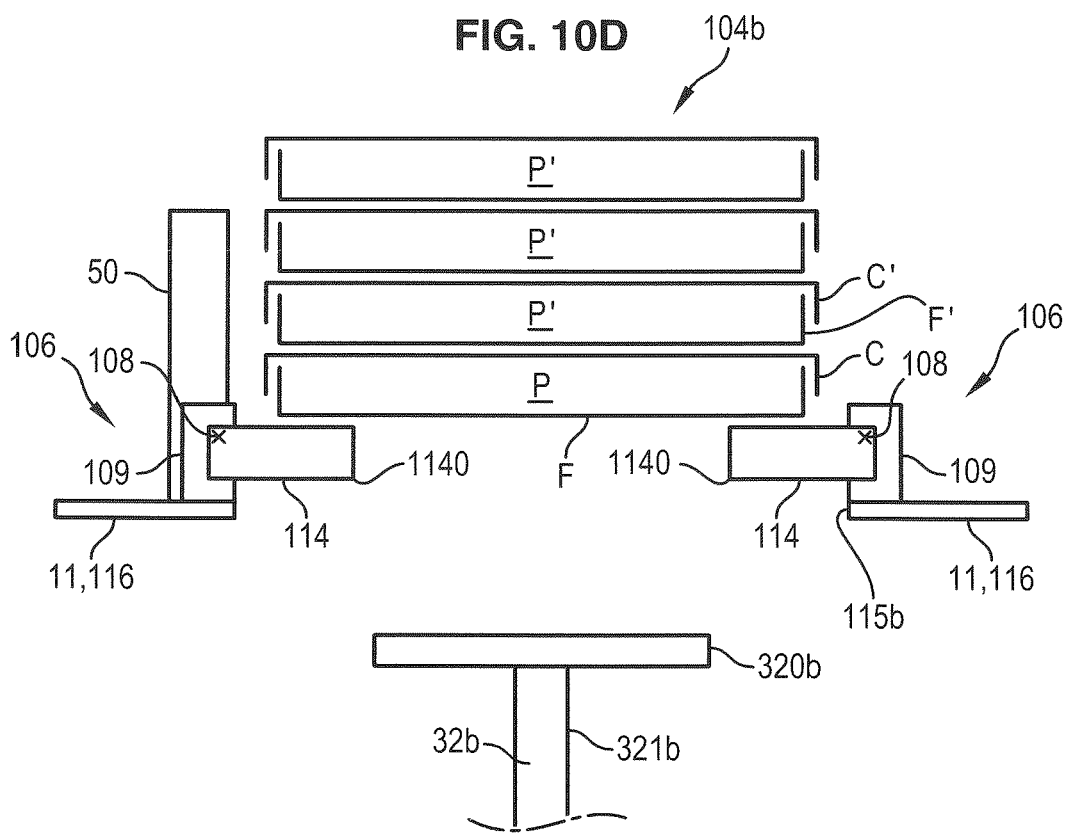

DEVICE AND METHOD FOR DISPENSING A PRODUCT INTO A PETRI DISH

CROSS-REFERENCE TO RELATED APPLICATIONS

This application is a National Phase Entry of International Application No. PCT/EP2010/061104, filed on Jul. 30, 2010, which claims priority to French Patent Application Serial No. 0955568, filed on Aug. 7, 2009, both of which are incorporated by reference herein.

BACKGROUND AND SUMMARY

The invention concerns a device for dispensing a prescribed product, in particular agar, into Petri dishes.

Petri dishes are small dishes of circular contour, in transparent plastic material, which contain a nutrient product such as an agar medium; they are used as medium for the development of cultures containing micro-organisms and are used in large number by analysis laboratories, in particular for medical research and in industry. Each Petri dish has a removable lid able to be placed over a bottom part that is less wide than the lid.

For product dispensing, a mechanical device is provided to open the dish and to transfer the open bottom part towards a product dispensing station which has a dispensing head comprising a nozzle through which product is dispensed into the bottom part. One of the problems raised by this dispensing station is related to the non-liquid consistency of the product dispensed thereat. Most often this product is viscous, in particular if it is agar. Owing to the viscosity thereof the product tends not to be uniformly distributed inside the bottom part of the Petri dish. This problem is further aggravated if only a small amount of product is dispensed into the bottom part of the Petri dish.

It is therefore sought to obtain a dispensing device for uniform distribution of product in the bottom part of a Petri dish, irrespective of the quantity of dispensed product and without the risk of spilling product outside the bottom part of the Petri dish. For this purpose, a first subject of the invention is a device for dispensing a prescribed product into at least one Petri dish, each Petri dish comprising a removable lid able to be arranged over a bottom part that is less wide than the lid, the device comprising means for bringing the Petri dish to a dispensing station, where the Petri dish is held with a space between its lid and its bottom part to allow the dispensing of the product via a product dispensing head comprising a nozzle outputting product towards the bottom part when the nozzle is in a dispensing position, characterized in that the device further comprises a piston comprising a tray for supporting the bottom part at the product dispensing station, and means for driving the tray in rotation around itself relative to the dispensing head, arranged to rotate the bottom part relative to the dispensing head situated in the position for dispensing product into the bottom part, in which the product outlet nozzle is arranged relative to the tray to dispense product into the bottom part set in rotation.

According to embodiments of the invention:

The speed at which the tray rotates around itself is between 10 and 100 rotations per minute.

The means for driving in rotation are designed to cause the tray to rotate around itself about a geometric axis of rotation, the nozzle comprises a product outlet end located away from the geometric axis of rotation of the tray set in rotation around itself, when in dispensing position.

The means for driving in rotation are designed to cause the tray to rotate around itself about a geometric axis of rotation, the outlet nozzle is arranged to dispense product into a region of the bottom part, said region being located at a distance from the geometric axis of rotation of the tray set in rotation, when in the dispensing position.

The tray comprises an upper surface that is concave from its centre towards its periphery to receive the bottom part of the Petri dish.

Said upper surface of the tray comprises a peripheral contacting part for contact with the bottom part of the Petri dish.

The tray comprises a recess in its centre on its upper surface.

The upper surface of the tray comprises a first peripheral contacting portion for contact with the bottom part of the Petri dish, this first contacting portion is in a material having greater adherence than the material of a second portion of the upper surface of the tray, surrounded by this first peripheral contacting portion.

The first peripheral contacting portion is a rubber material, whilst the second portion surrounded by this first peripheral contacting portion is metallic.

The transfer means comprise a transfer member for transferring the bottom part as far as a stop position at the dispensing station, the transfer member having an upper opening for supporting the lid of the Petri dish above a second lower opening for supporting the bottom part of the Petri dish, said tray being capable of passing through the openings to lift the bottom part of the Petri dish into the lid, passing through their respective support openings, when the transfer member is in the stop position at the dispensing station.

A column for the vertical guiding of Petri dishes is arranged above the piston to receive a Petri dish whose bottom part has been lifted up into its lid via said piston at the filling station, the piston being arranged to move the Petri dish with its bottom part lifted up into its lid from the transfer member to said column for vertical guiding of the Petri dishes, said column for vertically guiding of the Petri dishes comprising means to retain the Petri dish whose bottom part has been lifted into its lid and which has been brought by the piston.

A further subject of the invention is a method for dispensing a prescribed product into at least one Petri dish by means of the dispensing device such as described above, each Petri dish comprising a removable lid able to be placed over a bottom part that is of smaller width, a method in which the Petri dish is opened to hold its lid away from its bottom part, the bottom part is brought to a dispensing station, the dispensing head is placed in a dispensing position to dispense product into the bottom part positioned at the dispensing station, characterized in that the bottom part of the Petri dish is positioned on a piston comprising a tray rotating around itself, to cause the bottom part to rotate around itself throughout the entire time the product is dispensed into the bottom part from the dispensing head in dispensing position at said station.

BRIEF DESCRIPTION OF THE DRAWINGS

The invention will be better understood on reading the following description given solely as a non-limiting example with reference to the appended drawings in which:

FIG. 2A is a schematic, perspective view of a piston tray used in the device in FIG. 1;

FIG. 2B is a schematic, cross-sectional view of the tray in FIG. 2A;

FIG. 6A is a schematic, partial perspective view of the dispensing station in dispensing position, corresponding to FIGS. 1, 4 and 9C in one embodiment of the device according to the invention;

FIGS. 9A, 9B, 9C, 9D, 9E, 9F and 9G are partial magnified views of the device in FIG. 7, in different successive positions of operation for the filling of a Petri dish; and FIGS. 10A, 10B, 10C and 10D are schematic, profile views of part of the device in the preceding figures, at different positions.

DETAILED DESCRIPTION

Figure 1:
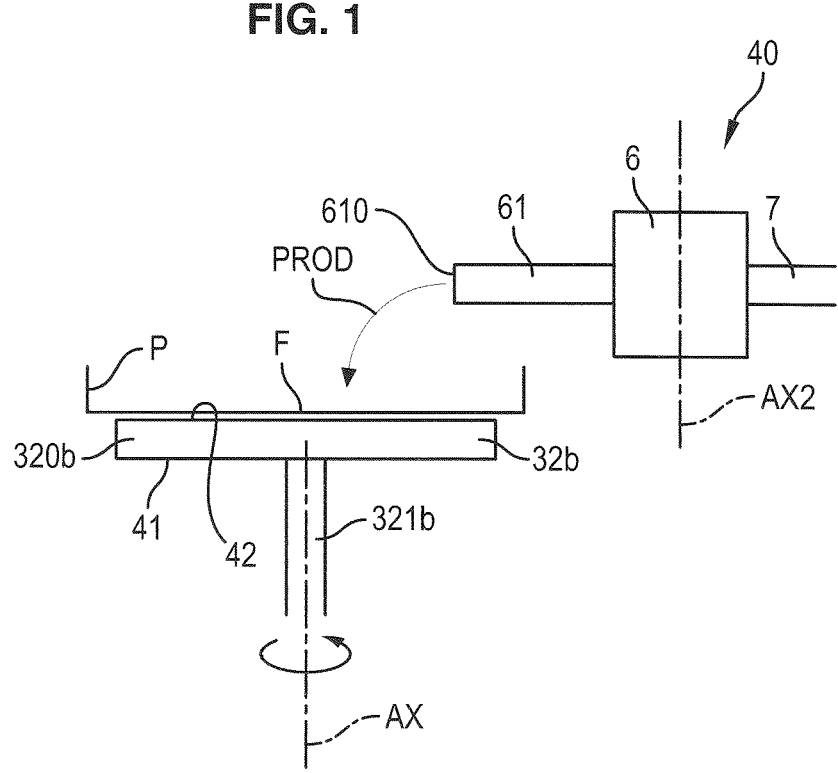
FIG. 1 is a schematic view of a dispensing device provided with a product filling station according to the invention.

In FIG. 1 a product dispensing station 40 for dispensing product into a bottom part F of a Petri dish P is illustrated. This product is agar for example. As shown in the other figures, each Petri dish P comprises a bottom part F and a lid C. The station 40 comprises a product dispensing head 6 having an outlet nozzle 61 for outputting product towards the bottom part F.

Figure 5:
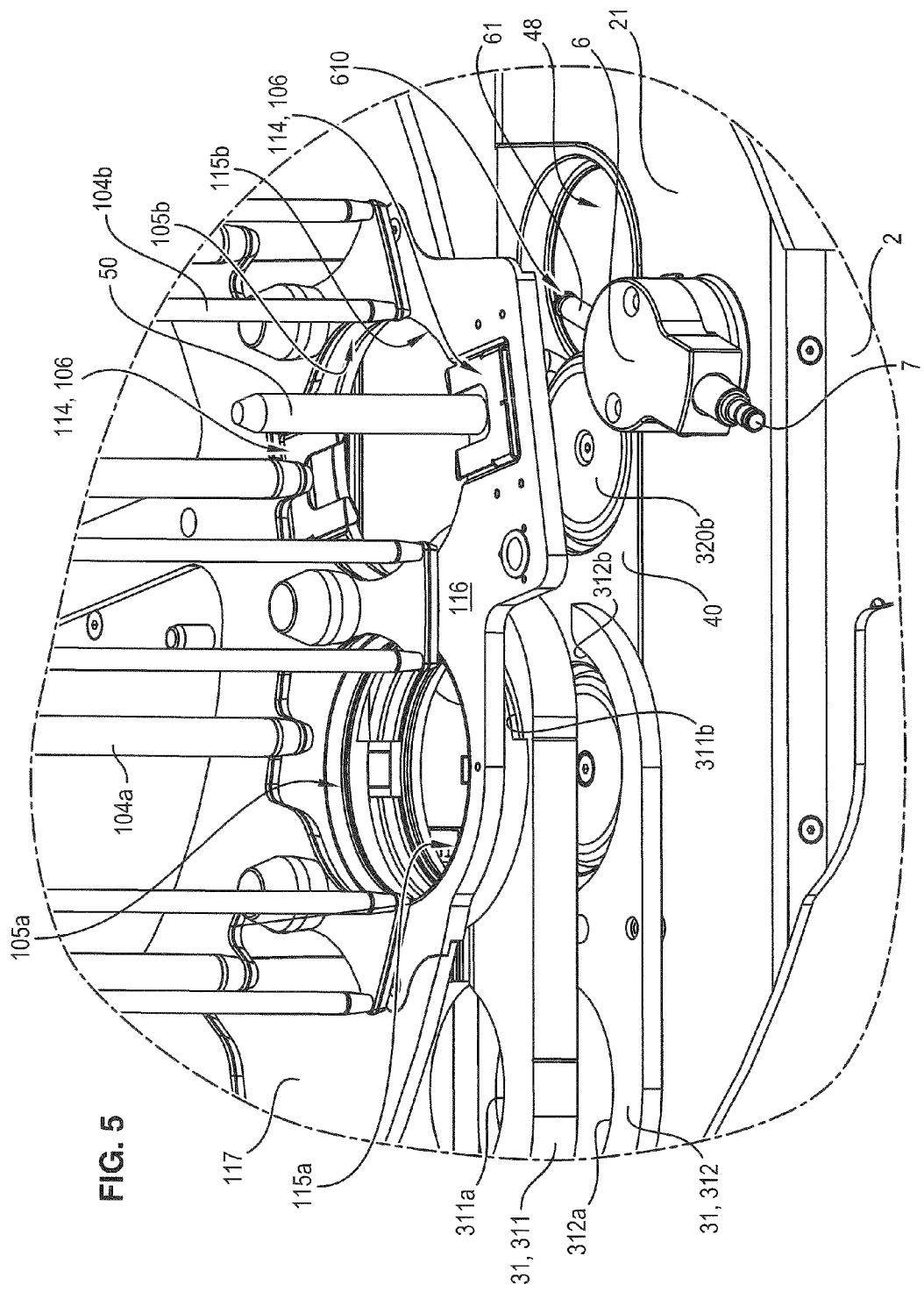
FIG. 5 is a schematic, partial perspective view of the dispensing station in retracted position corresponding to FIG. 9B, in one embodiment of the device according to the invention.
Figure 6B:
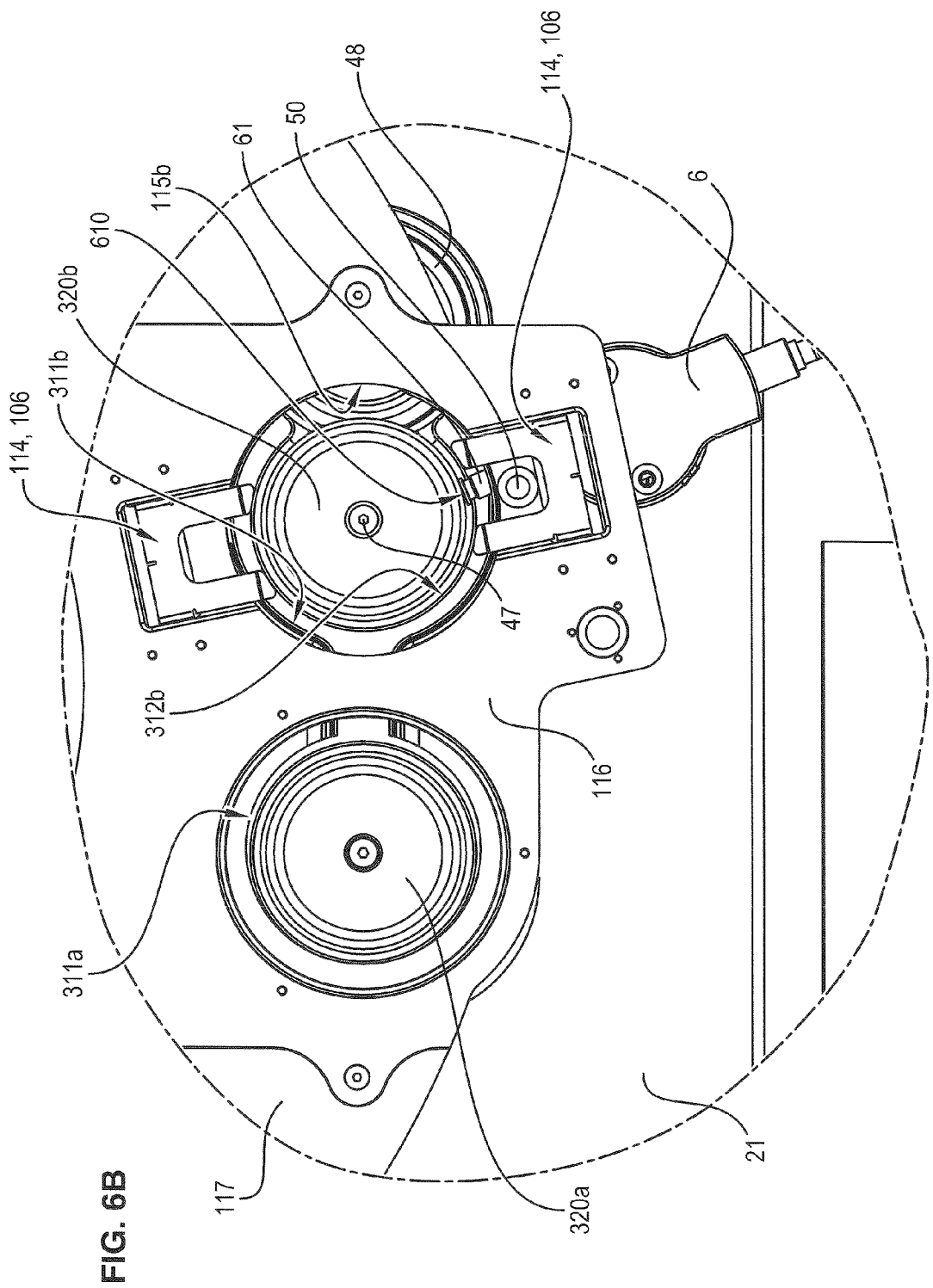
FIG. 6B is a schematic, partial overhead view of the dispensing station in FIG. 6A, in one embodiment of the device according to the invention.
Figure 7:
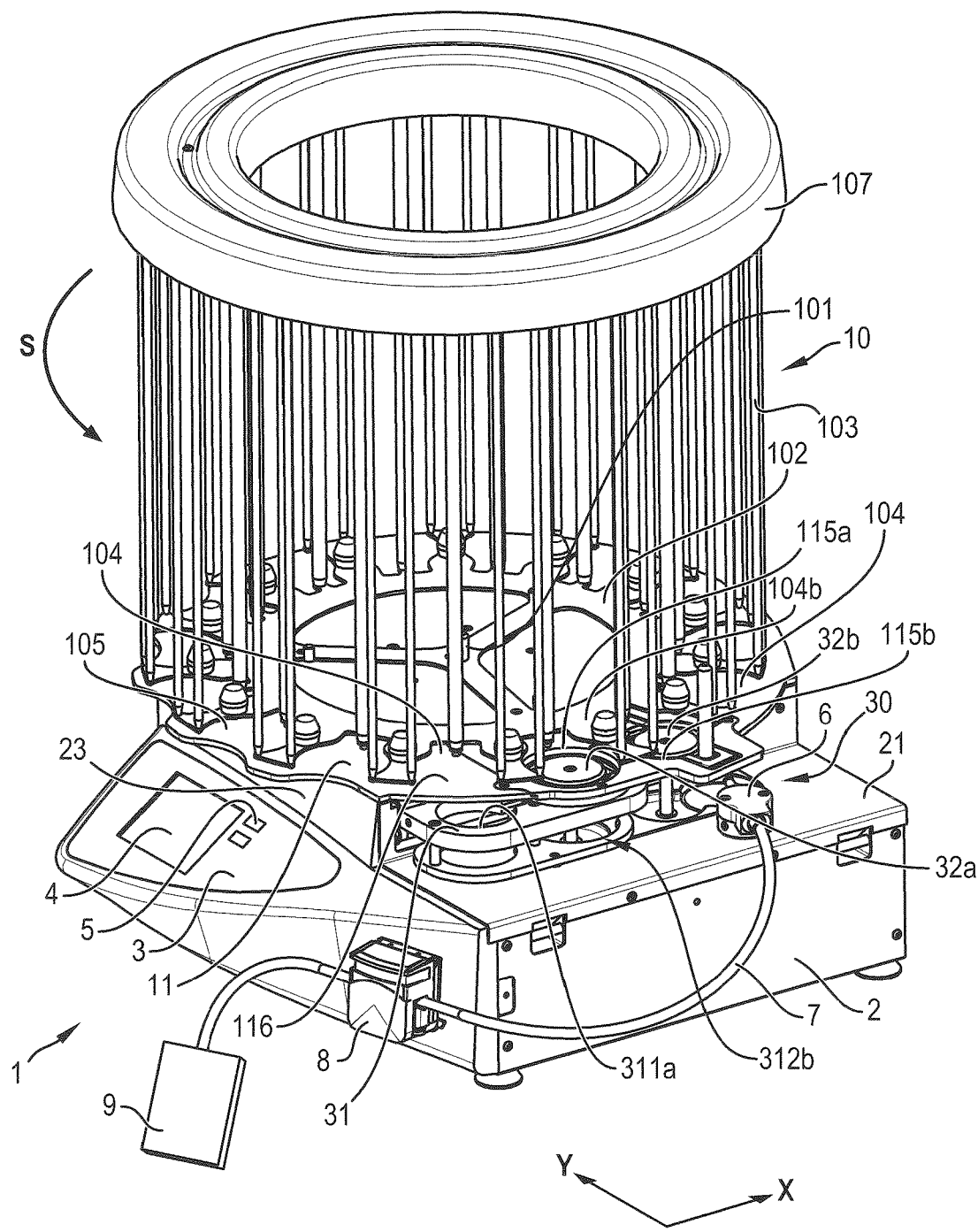
FIG. 7 is a schematic, perspective view of one embodiment of the a machine using the dispensing device according to the invention.

The dispensing station 40 also comprises a piston 32*b* comprising an upper tray 320*b* for receiving the bottom part F of a Petri dish. The bottom part F of the Petri dish is brought by suitable means onto the tray 320*b* where product is dispensed therein via the head 6. These means for moving the bottom part F of the Petri dish as far as the dispensing station 40 are for example the means in the embodiment described with reference to FIG. 5 et seq. These means allow opening of the Petri dish P so as to leave a space between its bottom part F and its lid C. Therefore, at the dispensing station 40, the head 6 can be placed in a product dispensing position in which the outlet nozzle 61 has an outlet tip 610 located above the open dish bottom part F positioned on the tray 320*b*.

The tray 320*b* is connected to means for driving the tray 320*b* in rotation around itself. For example, the tray 320*b* is connected on its lower side 41 to a central pin 321*b* secured to the tray 320*b*. By causing the central pin 321*b* to rotate around itself, the tray 320*b* is caused to rotate around itself. An electric motor, via a belt and gear, is used to drive the central pin 321*b* and hence the tray 320*b* to rotate around itself. The tray 320*b* is of general planar shape, e.g. horizontal, and the rotating of the tray 320*b* around itself takes place over this horizontal plane.

Means for controlling the head 6 are provided to feed product into the nozzle 61 in the product dispensing position when the tray 320*b* is rotating. The rotating of the tray around itself allows the product dispensed by the nozzle 61 to be distributed over the entire surface of the bottom part F of the Petri dish, whilst avoiding spillage of the product outside the bottom part F. Therefore the bottom part F is maintained in rotation around itself throughout the entire duration of dispensing of product from the nozzle 61 in dispensing position.

The spatial distribution of the product in the bottom part F of the Petri dish is therefore made more uniform, with minimum space requirement, whilst avoiding having to agitate the bottom part F and by simultaneously dispensing product via the head 6 into the bottom part F, providing savings in time. Therefore, the dispensing process is not delayed by setting the tray in rotation 320*b* during the product dispensing step via the head.

Synchronization means for example are provided, to synchronize the changeover of the head 6 to the dispensing position and the feeding of product into the nozzle 61, with the setting in rotation of the tray 320*b*. The tray 320*b* is set in rotation at least for the time during which product is dispensed via the nozzle 61 of the head 6 in dispensing position. The head 6 is mobile between a retracted position shown in FIG. 3 in which the nozzle does not lie above the dish bottom part F and the tray 320*b*, and in which the product is not dispensed by the head 6, and the dispensing position illustrated in FIGS. 1 and 4, for example by rotation about another vertical axis AX2. Automated control means are provided to move the head 6 between each of these positions.

In the dispensing position, the end 610 of the nozzle 61 is located for example above a point of the tray 320*b* that lies away from the geometric axis of rotation AX about which the tray 320*b* rotates so that, under the centrifugal force of rotation, the dispensed product as illustrated by the arrow PROD moves away from the centre located on the axis of rotation. On account of the horizontal dispensing rate of the product out of the end 610, it is the region in which the product falls onto the bottom part F which is able to lie distant from the centre located on the rotation axis AX, as illustrated by the arrow PROD showing the trajectory of the product dispensed by the head 6.

The rotating speed of the tray is between 10 and 100 rotations per minute for example, and in particular between 50 and 90 rotations per minute. In one embodiment, the speed of rotation of the tray 320*b* is 75 rotations per minute for example for an product formed of agar.

In the embodiment illustrated in FIGS. 2A and 2B, the upper surface 42 of the tray 320*b* used to receive the underside of the bottom part F is slightly concave for example from its periphery towards its centre. It has been observed that the bottom parts F of Petri dishes may have a slightly convex downward central bulge on their lower surface via which they necessarily rest on any strictly planar surface. In this case, only one other peripheral point of the dish bottom part F also rests on the planar surface in addition to the central bulge. These point contacts of the bottom part F with a planar surface are detrimental to the driving in rotation by a strictly planar tray. The concave shape of the upper surface 42 of the tray 320*b* allows the central downwardly bulged part of the bottom part F to be housed in the centre of the tray 320*b* ensuring that the contact surface of the bottom part F with the tray 320*b* extends over the entire lower periphery of the bottom part F. For this purpose, the upper concave surface 42 of the tray 320*b* comprises for example a recess 43 to receive the centre of a bottom part F of a Petri dish. The vertical rotation axis AX of the tray 320*b* rotating around itself passes substantially via this recess 43. The recess 43 extends for example from the upper surface 42 to the lower surface 41 of the tray 320*b* and therefore forms a through hole. The surface 42 therefore has a positive slope from the centre of the tray 320*b* towards its periphery 44.

The tray 320b is secured to the pin 321b by a screw 47 for example housed in the hole 43 that is for example of flattened cone shape tapering from top downwards to retain the screw 47 inside the hole 43. The upper peripheral surface 44 of the tray 320b is for example in a separate material from part 45 thereof which it surrounds, and is for example in a material ensuring better adherence by contact with the bottom part F of a Petri dish than part 45. Part 44 is for example in a rubber material, whilst part 45 is for example metallic.

Therefore, in general, the bottom part F of a Petri dish mostly rests via a peripheral surface on the tray 320b to improve driving in rotation. The tray 320b is less wide than the bottom part F of the Petri dish P.

Figure 3:
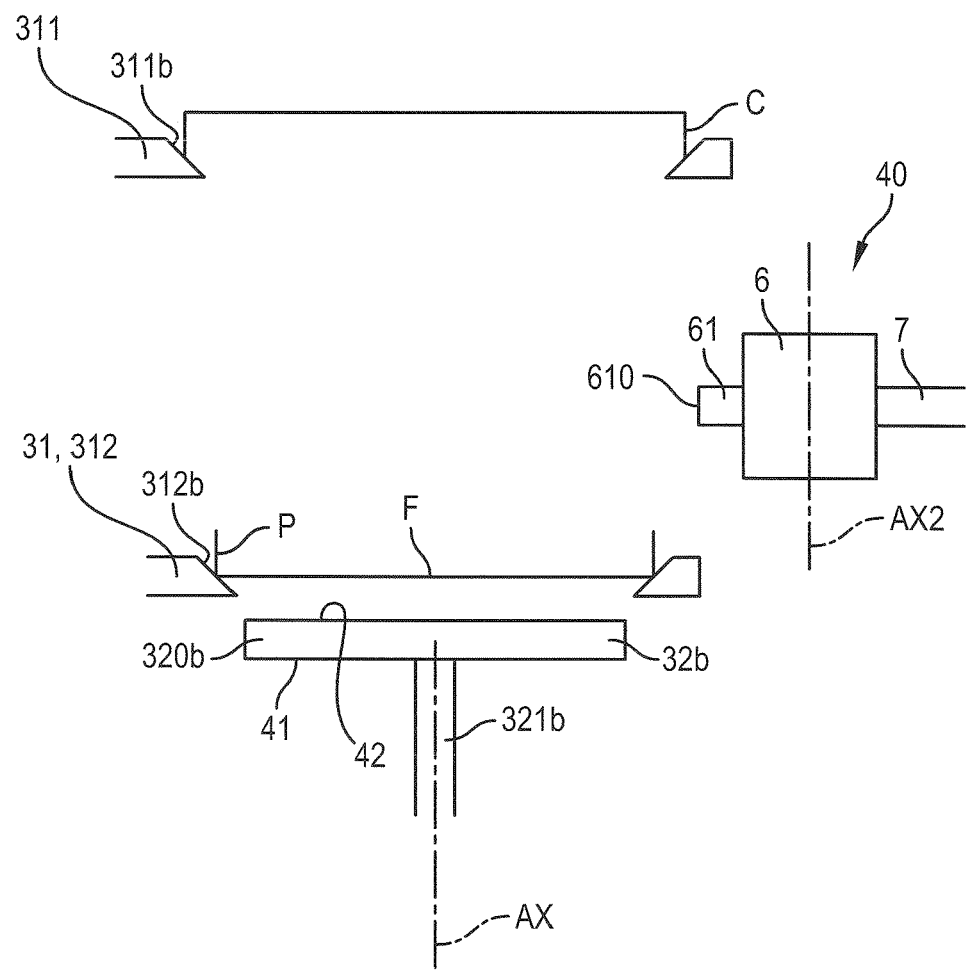
FIG. 3 is a schematic side view of the piston in a lowered position underneath the bottom part of a Petri dish, in one embodiment of the device according to the invention.
Figure 4:
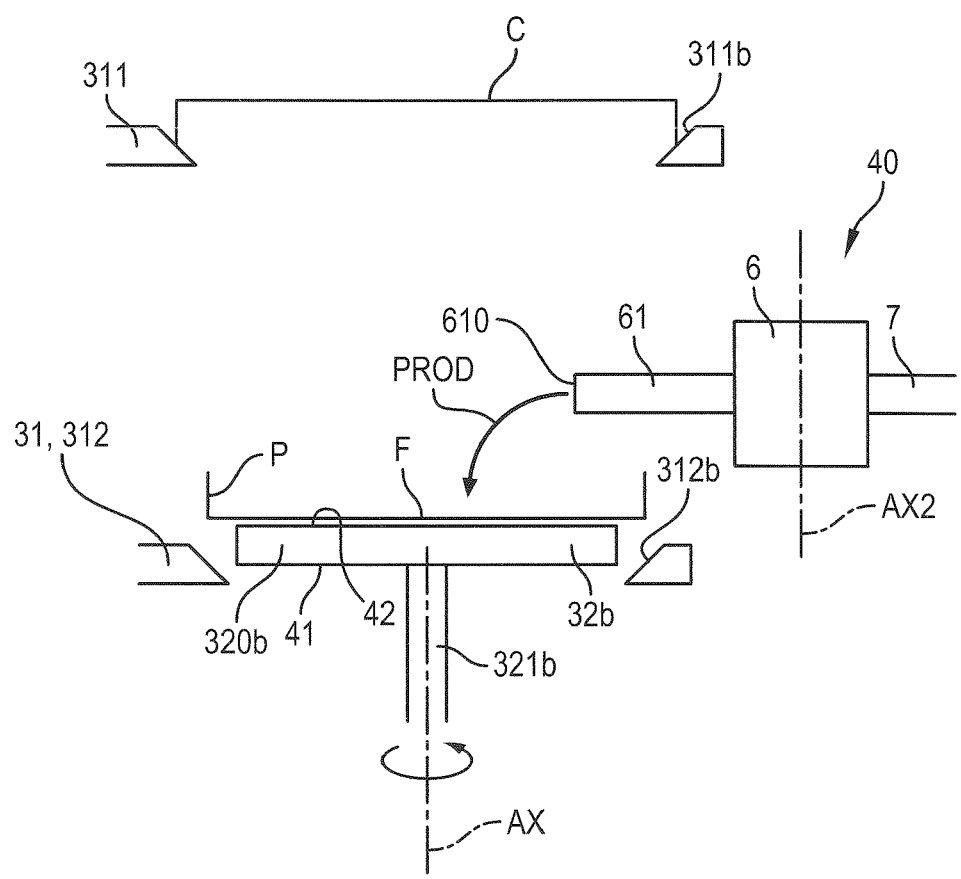
FIG. 4 is a schematic side view of the piston in an elevation position of the bottom part of a Petri dish for the dispensing of product, in one embodiment of the device according to the invention.

In FIGS. 3 and 4 and the following figures, the device transferring the bottom part F to the product dispensing station comprises a shuttle 31 having a top-plate 311 for supporting the lid C of a Petri dish P and a bottom plate 312 for supporting the bottom part F of the same Petri dish P. The top plate 311 comprises a second upper opening 311b used for passing the bottom part F of a Petri dish and for retaining the lid C of a Petri dish. The second upper opening 311b has a width Lb larger than that of the bottom part F of a Petri dish but smaller than that of its lid C. The second lower opening 312b acts as support for the bottom part F of the Petri dish and has a width smaller than the width of this bottom part F. The second openings 311b and 312b are therefore called supporting openings for a Petri dish P.

In FIGS. 1, 3 and 4, the shuttle 31 has brought the bottom part F and the lid C as far as the dispensing station 40 and is in a stop position at the dispensing station 40, which in the remainder hereof is called the second stop position. When the shuttle 31 arrives at this second stop position at the dispensing station 40, the dispensing head 6 initially lies in the retracted position illustrated in FIG. 3, the bottom part F rests on the second lower opening 312b of the plate 312, the lid C rests on the second upper opening 311b and the piston 32b is in a lowered position so that its tray 320b lies underneath the bottom plate 312. Then, the tray 320b of the piston 32b is lifted through the lower opening 312b via means for vertical driving of its pin 312b to lift the bottom part F to a first elevation position at a distance above this lower opening 312b as illustrated in FIG. 4. Once the piston is in this first elevation position, the tray 320b is set in rotation around itself as described above. At the same time, or after lifting of the piston 32b, the head 6 is moved from the retracted position to the dispensing position illustrated in FIG. 4 to dispense then product into the bottom part F set in rotation by the rotating tray 320b. Then, after stopping the dispensing of the product via the head, the head 6 changes from the dispensing position to the retracted position which lies away from the travel direction of the bottom part F and tray 320b. The tray 320b supporting the bottom part F containing the dispensed product P is then moved upwardly from the elevation position in FIG. 4 to pass through the second upper opening 311b of the top-plate 311 and the dish bottom is inserted upwardly into the lid C positioned thereat so as to close the lid C over the bottom part F. The lid C thus closed over the bottom part F is then again lifted by the tray 320b as far as a receiver column as is described below. In the retracted position, the nozzle 61 and its outlet end 610 lie above a collector vessel or recess 48 provided to collect any drops which may drip from the nozzle 61 after dispensing into the bottom part F, thereby preventing the soiling of the remainder of the device and in particular all the mechanisms thereof used to move the shuttle 31, the piston(s) and the head 6.

A description will now be given of other parts of an embodiment of the dispensing device. In the remainder hereof, the piston 32b is the second piston 32b, the tray 320b is the second tray 320b.

In FIGS. 5, 6A, 6B, 7, 8, 9A, 9B, 9C, 9D, 9E, 9F, 9G, 10A, 10B, 10C, 10D, the dispensing device 1 comprises a base 2 in the form of a casing. The base 2 comprises a front side 22 on which there is a control panel for the device, provided for example with a control screen 4 and one or more control buttons 5 or any other interface 5, enabling the user to control the automatic functioning of the device 1. On the base 2 there are provided means 6 for dispensing a prescribed product which may for example be liquid agar or an agar medium. This dispensing means 6 is for example in the form of a head 6 rotating about a vertical axis on an upper side 21 of the base 2, the head comprising the nozzle or product outlet end 61. This dispensing means 6 is supplied with product via a tube 7 connected to means 8 for feeding the means 6, this means 8 being formed for example of a peristaltic pump 8 arranged on the base 2, for example on its front side 22, the other end of the tube 7 being connected to a supply 9 of the product.

The base 2 comprises an upper part 23 that is raised relative to the upper side face 21, adjacent to this upper part 23. The raised part 23 carries a carousel 10 for storing Petri dishes. The carousel 10 is on the base 2 and rotates relative to a central vertical shaft 101, on part 23 of the base 2. The carousel comprises a lower ring 102 carrying means 103 for storing Petri dishes in stacks. These means 103 delimit a plurality of vertical columns 104 for housing and guiding stacks of Petri dishes, and for this purpose they comprise rods 103 or any other means for vertical guiding of the Petri dishes. A removable upper ring 107 is provided to cap the means 103. Each column 104 leads downwardly via an opening 105 for the passing of a Petri dish into the lower ring 102. Therefore, these openings 105 have a wider diameter than the Petri dishes. The openings 105 of the columns 104 are distributed equidistantly from the central rotation shaft 101 and are equiangular on the lower ring 102. The openings 105 are peripheral to the lower ring 102 for example and in the form of notches of the ring 102. The height of the guiding means 103 is designed to receive, in each column 104, a stack of several Petri dishes in prescribed number up as far as the ring 107. Each Petri dish P is inserted in a column 104 with its lid C placed over its bottom part F so that the dish is removably closed, the Petri dishes P as is known per se having a lid C that is wider than their bottom part F as is illustrated in the figures. When the Petri dish is closed, the rim of the lid lies outside the rim of the bottom part.

Underneath the lower ring 102 of the carousel and on the base 2, there is a horizontal guide plate 11 for horizontal guiding of the Petri dishes when they are in the carousel 10. The shaft 101 of the carousel is connected to means for driving in rotation located in the base 2 to cause the carousel 10 to rotate horizontally about this vertical shaft 101. The horizontal guide plate 11 is secured to the raised part 23 and comprises a part 116 located above the upper surface 21 and underneath several columns 104 of the carousel 10. The horizontal guide plate 11, in part 116, comprises a first opening or passageway 115a and a second opening or passageway 115b having the same spatial distribution as two lower openings 105 of the carousel 10, to allow the passing of a Petri dish through these openings 105, 115a, 115b. For better compactness, the distance between the first opening 115a and the second opening 115b of the plate 105 corresponds to the distance between two first and second respective lower adjacent openings 105a and 105b of the carousel 10.

The first and second openings 115a and 115b of the plate 11 are located above a station 20 allowing the unstacking of the empty Petri dishes, the opening thereof, the dispensing of product into their bottom part, their closing and their re-stacking in the filled state. The station 20 is located on the upper side 21 of the base 2.

The station 20 comprises a system 30 for moving the Petri dishes one by one in the empty state from underneath the column 104b into the opening 105b through the opening 115a, via a horizontal transfer member 31 and two first and second pistons 32a, 32b moving vertically respectively under the second and first columns 104a, 104b. Each piston 32a, 32b comprises an upper tray 320a, 320b fixed to a lower vertical rod 321a, 321b connected in the base 2 to vertical driving means to cause the pistons 22a, 22b to be raised and lowered. The transfer member 31 is a shuttle 31 performing a back and forth movement in translation along a longitudinal horizontal direction X.

Figure 8:
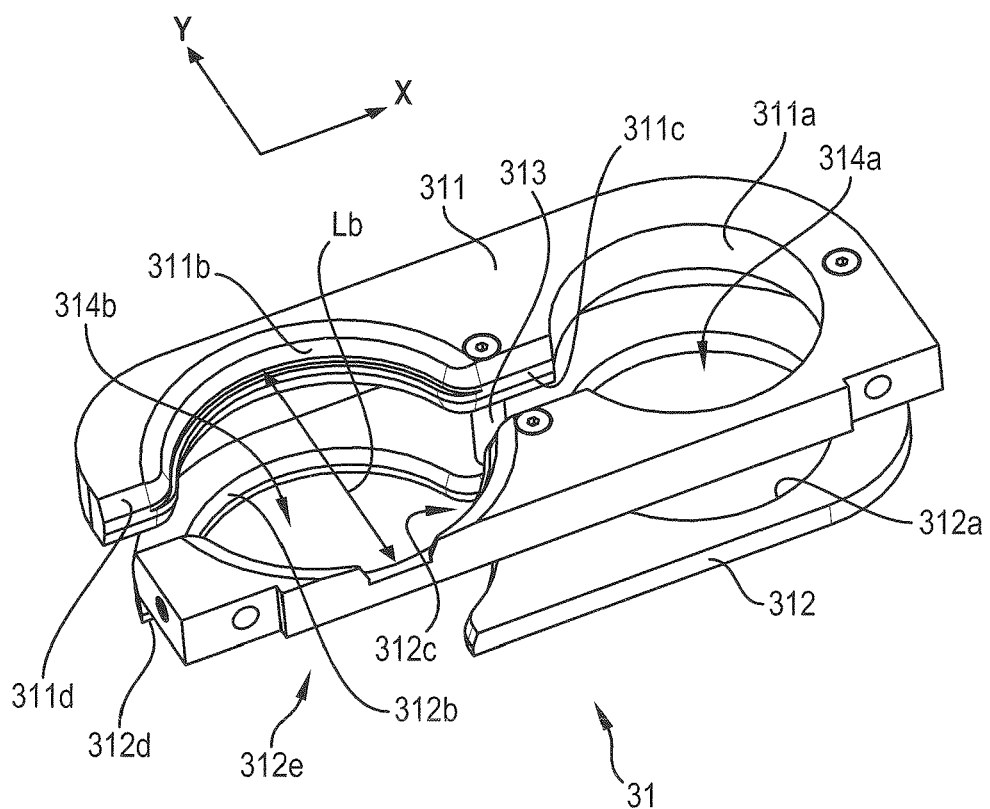
FIG. 8 is a schematic, perspective view of part of the device in FIG. 7.

One embodiment of the member 31 is illustrated in FIG. 8 and is described in more detail below. In this embodiment, as illustrated in FIGS. 9A, 9B, 9C, 9D, 9E, 9F and 9G, the pistons 32a and 32b have simultaneous vertical translation movements so that their trays 320a, 320b lie at the same height as each other. This makes it possible, in this case, only to have one motor for both pistons 32a and 32b for driving in vertical translation. In the illustrated embodiment, the first and second pistons 32a and 32b have the same synchronized movement, and both lie at the same time in the top position (FIGS. 9A and 9G), in bottom position (FIGS. 9B, 9C, 9D) or in elevated position (FIGS. 9E, 9F).

The shuttle 31 comprises a top plate 311 and a bottom plate 312 joined to each other via spacers 313. Evidently, the shuttle 31 can be made in a single piece. The bottom plate 312 is used for guiding the shuttle 31 in translation on the surface 21 and for stabilizing the shuttle 31 on this surface 21. The means 60 for driving the shuttle 31 in translation are lateral means and are housed in the base 2 underneath the raised part 23.

In the figures, the top plate 311 comprises a first upper opening 311a and the second upper opening 311b which respectively lie above a first lower opening 312a and the second lower opening 312b of the bottom plate 312. The first lower and upper openings 311a and 312a are used for passing of the first tray 320a of the first piston 32a and are wider than the latter.

In addition, the top plate 311 comprises a connecting passage 311c between the first upper opening 311a and the second upper opening 311b, to allow the passing of the rod 321a of the first piston 32a between these openings 311a and 311b. The passage 311c has a transverse horizontal width greater than that of the rod 321a of the first piston 32a. The bottom plate 312 comprises a passage 312c connecting the first lower opening 312a and the second lower opening 312b to allow the passing of the rod 321a of the first piston 32a between these openings 311a and 311b. The passage 312c has a transverse horizontal width wider than that of the rod 321a of the first piston 32a.

In FIG. 8, the shuttle 31 extends in a longitudinal horizontal direction X which is the horizontal direction extending between the two openings 115a and 115b of the plate 105. The transverse horizontal direction Y is the direction perpendicular to the longitudinal direction X.

The plate 11 comprises means 106 for retaining and passing Petri dishes P, P' stacked above the second opening 115b. These means 106 are mobile between a first retaining position of a stack of Petri dishes P' retained on the underside above the opening 115b in the column 104b, as is illustrated in FIGS. 10A, 10C and 10D, and a second release position for the released passing of the Petri dishes through the opening 115b as is illustrated in FIG. 10B. These Petri dishes P' already located in the column 104b comprise a lid C' placed over a bottom part F'. The means 106, at several points for example around the opening 115b, comprise a lug 114 hinged by a horizontally rotation axis 108 on a support 109 secured to the part 116 in the vicinity of the opening 115b, for example two diametrically opposite lugs 114. In the retaining position shown FIGS. 9B, 9C, 9D and 10A, the lugs 114 extend above the opening 115b to delimit between them a width that is smaller than the width of the bottom part F' of the Petri dishes P' to support the bottom part F' of the lowermost dish, this width allowing passing of the tray 320b of the piston 32b between the lugs 114 and being wider than the width of this tray 320b.

When the tray 320b having upon it a Petri dish P, with its lid C placed over its bottom part F, passes from bottom upwards through the opening 115b towards the column 104b in FIG. 10B, the lid C of this dish P lifted by the tray 320b lifts up the lugs 114 to cause them to rotate outwardly. During the rising of the tray 320b in FIG. 10B, the tray 320b is at a height relative to the opening 115b such that the lugs 114, via their free end 1140 distant from the axis 108, bear laterally against the Petri dishes P, P'. Means are provided to compel the lugs 114 to be applied towards the retaining position, for example under gravity or due to the positioning of their pin 108 in the lug 114, or via a spring or other positive return means.

In FIG. 10C, the tray 320b changes to a second elevation position above the free end 1140 which had been resting against the Petri dishes P, P' supported by the tray. This second elevation position corresponds to FIGS. 9E and 9F. Therefore the end 1140 of the lugs falls back to the retaining position towards the opening 115b. The second elevation position in FIG. 10C is above the first elevation position illustrated in FIG. 4. When, from FIG. 10C to FIG. 10D, the piston 32b is lowered, its tray 320b passes between the lugs 114 lying in retaining position, then passes through the opening 115b whereby the stack of Petri dishes P, P' is deposited on the lugs 114 in retaining position.

The functioning of the device is the following. FIGS. 9A, 9B, 9C, 9D, 9E, 9F and 9G illustrate the trajectory of an empty Petri dish P, i.e. comprising a lid C and a bottom part F, which is the dish that is lowermost in the column 104a.

In FIGS. 5, 9A, 9B, 9F and 9G the shuttle 31 lies in a first stop position. In FIGS. 6A, 6B, 9C, 9D and 9E the shuttle 31 is in a second stop position. In the first stop position P1, the supporting openings 311b and 312b of the shuttle 31 lie under the first opening 115a, which itself lies under an opening 105a of a column 104a of empty, closed Petri dishes. In the first stop position P1, the shuttle 31 is arranged on the other side of the second piston 32b, a solid part 117 of the plate 11 being positioned between the carousel 10 and the first upper opening 311a of the shuttle 31.

In the second stop position P2, the first openings 311a and 312a of the shuttle 31 lie under the first opening 115a and under the first column 104a. In the second stop position, the second openings 311b and 312b of the shuttle 31 lie under the second opening 115b and under the second column 104b. In the embodiment illustrated in the figures, the shuttle 31, as stop position, solely comprises the first stop position P1 and the second stop position P2.

Figure 9B:
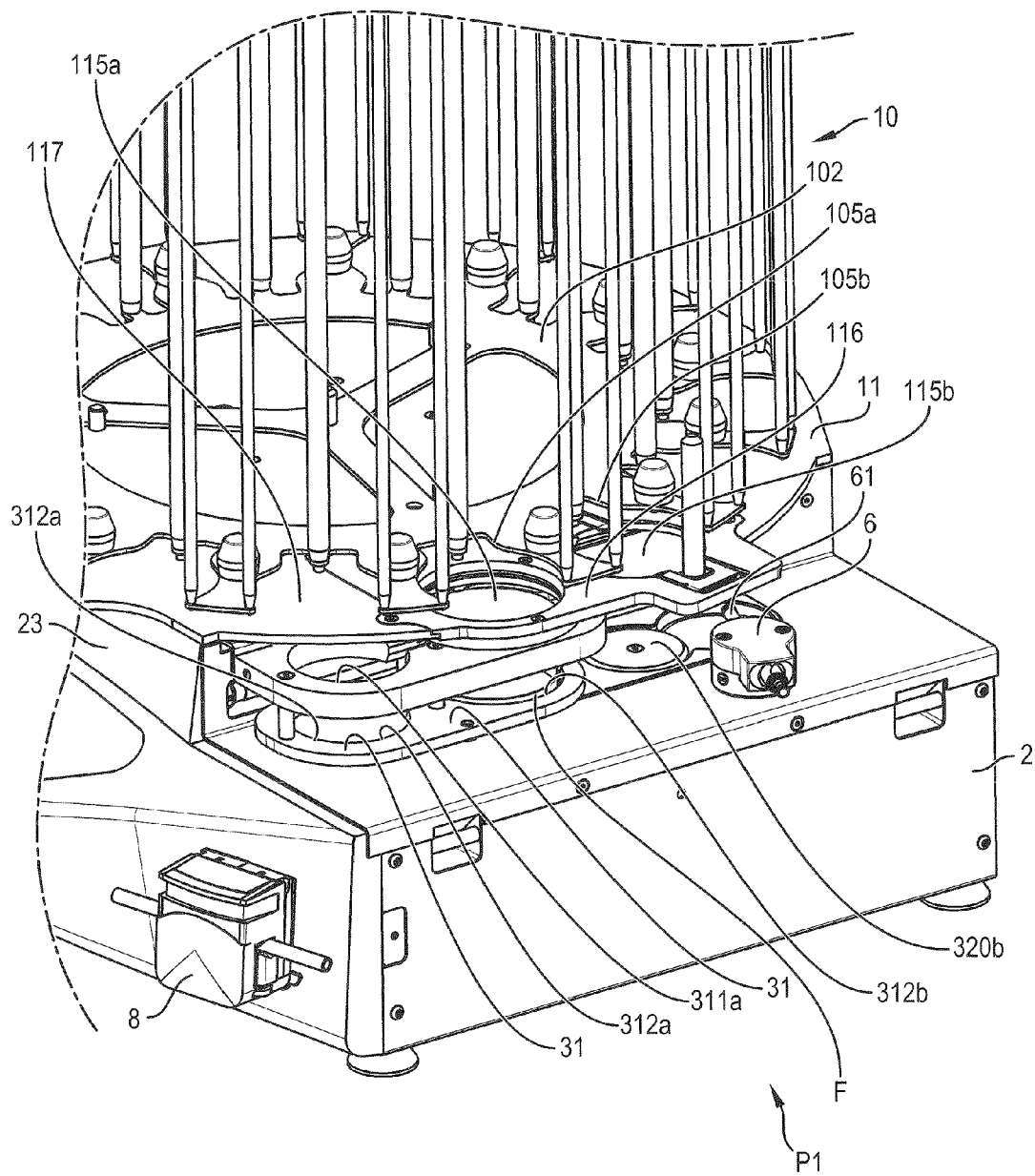
Figure 9C:
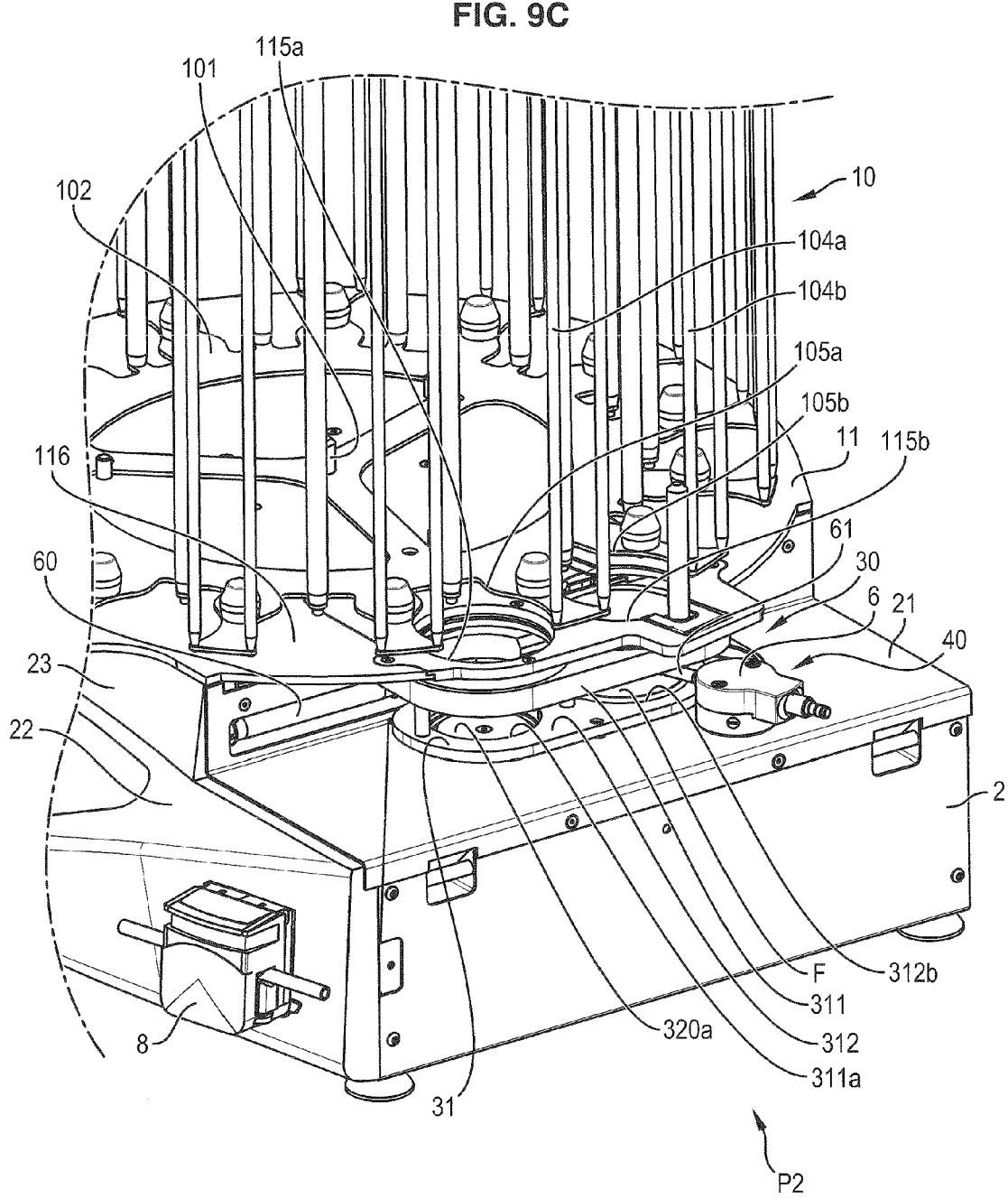
Figure 9D:
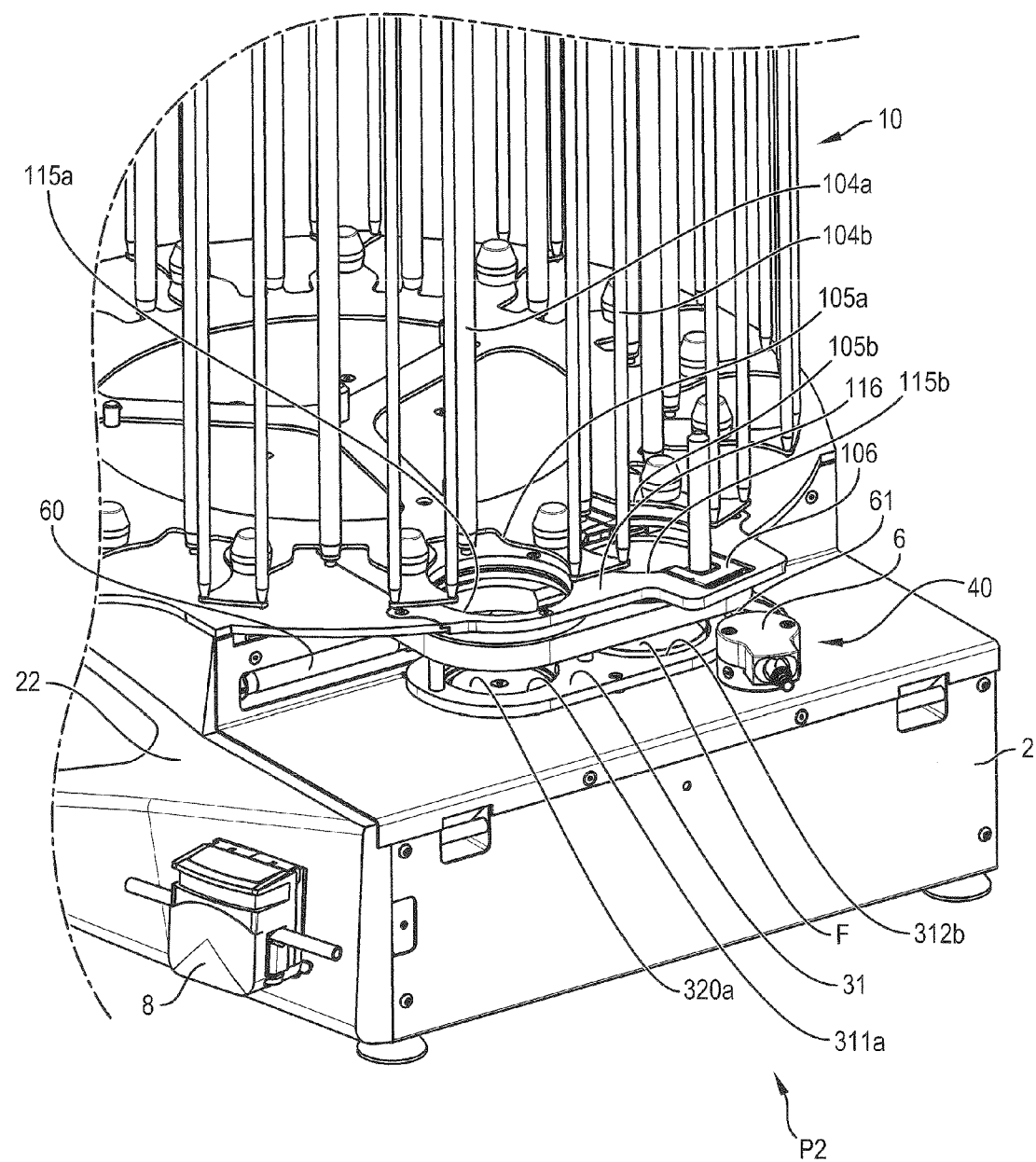
Figure 9E:
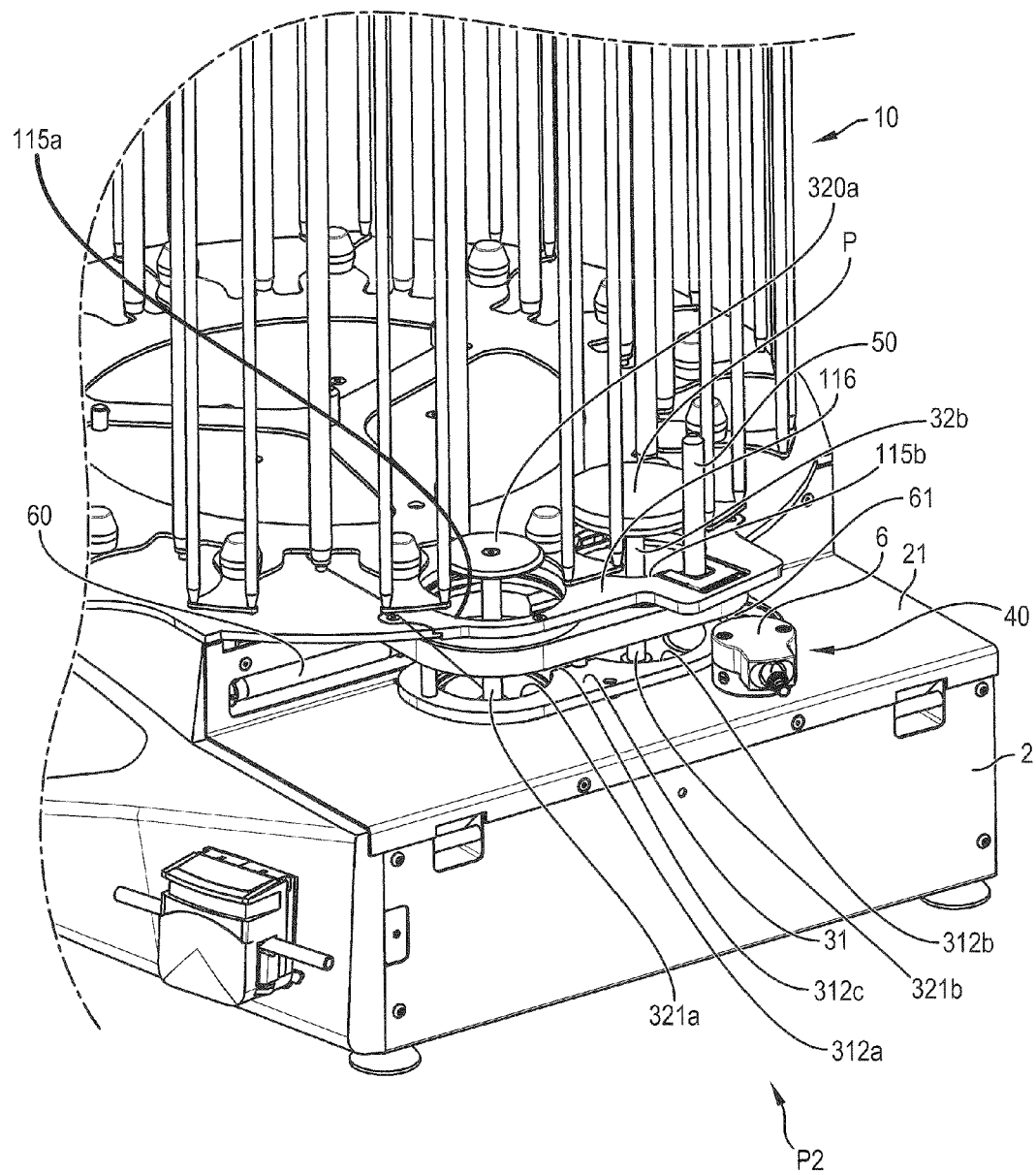
Figure 9F:
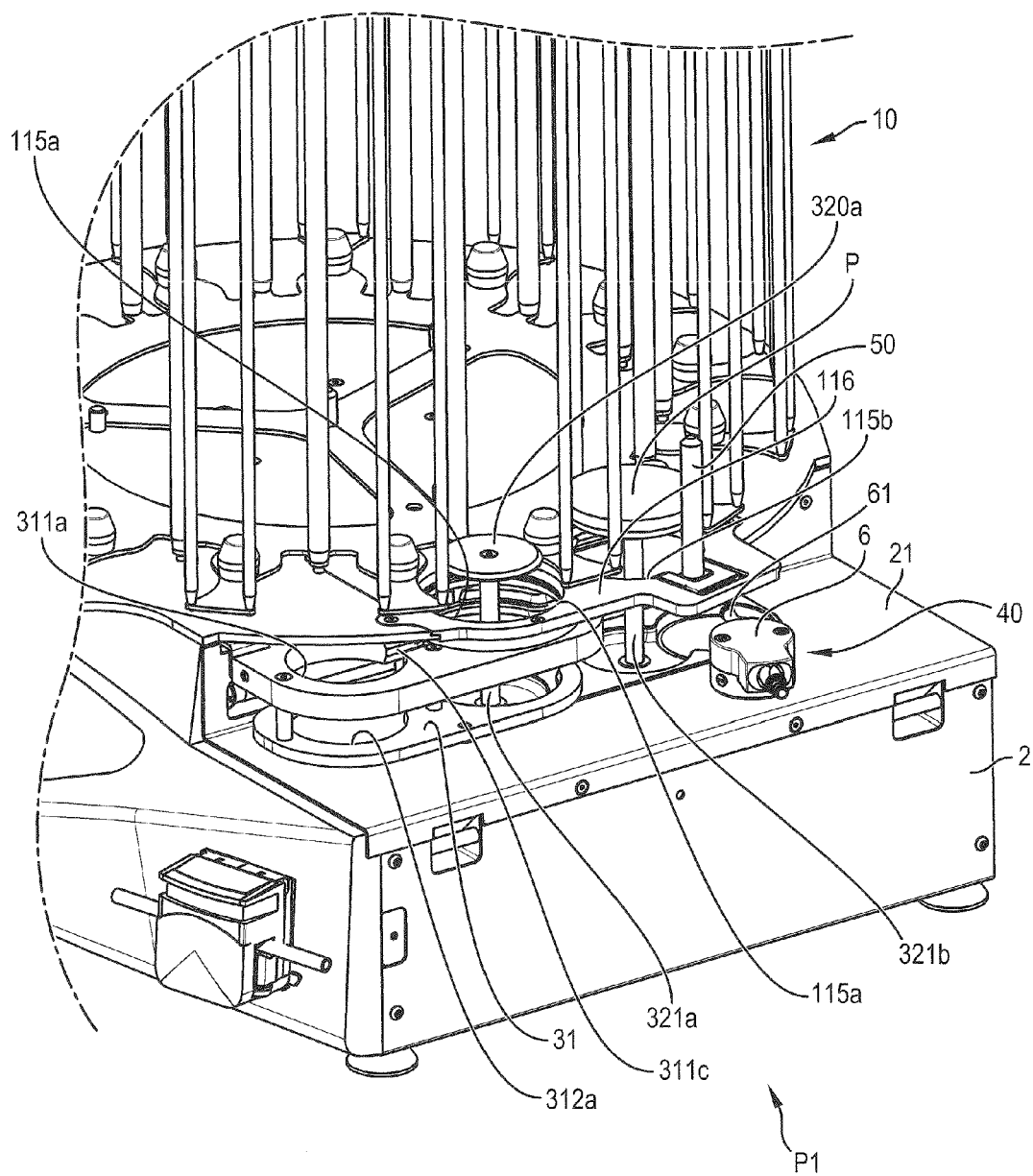

In FIG. 9A, the first tray 320a of the first piston 32a supports the first stack 104a of Petri dishes P in the first column 104a above the second openings 312b and 311b, the rod 321a passing through these openings 312b and 311b. The piston 32a is then lowered though the second openings 311b and 312b of the shuttle 31 to bring the lid C of the Petri dish P at the bottom of the column 104a onto the second upper opening 311b and to bring the bottom part F of the dish P onto the second lower opening 312b, to arrive at the position illustrated in FIG. 9B. In FIGS. 9B, 9C, 9D the trays 320a, 320b of the pistons lie underneath the shuttle 31 for example in housings arranged in the surface 21.

In FIGS. 9A and 9B, the product dispensing means 6 lie in the retracted position in which the nozzle 61 lies neither above the opening 312b nor above the piston 32b. In this retracted position, the nozzle 61 leaves the passageway free between the second lower opening 312b and the second upper opening 311b and in this case lies outside the direction of travel of the piston 32b.

The shuttle 31 is then moved via longitudinal, horizontal translation along direction X to arrive at the second stop position illustrated in FIG. 9C. The dispensing means 6 changes to the dispensing position to dispense product, for example by rotation of the dispensing head 36 so as to bring its dispensing nozzle 61 between the top-plate 311 and bottom-plate 312 above the second lower opening 312b and hence above the dish bottom part F located thereat in FIG. 9C.

The bottom part F supported on/in the second lower opening 312b and the lid C supported on/in the second upper opening 311b lie underneath the second opening 115b of the fixed plate 11 and underneath the second column 104b. Automated means provided in the base 2 then cause controlling of the feed means 8 to cause product to arrive in the dispensing means 6, this product then being dispensed by these means 6 above the second upper opening 312b into the bottom part F of the Petri dish located thereat. Then, in the position illustrated in FIG. 9D, the dispensing means 6 are returned to their position distant from the second lower opening 312b or retracted position.

In FIG. 9E, the pistons 32a and 32b move to the elevation position in FIG. 10C above the shuttle 31 and in the column 104b. The second piston 32b therefore first lifts the bottom part F located in the second lower opening 312b, then lifts the bottom part F into the lid C located in the second upper opening 311b, which closes the Petri dish P whose bottom contains product which has been dispensed therein by the means 6, then lifts the dish P thus filled and closed into the second column 104b via the second opening 115b and the second opening 104b of the carousel 10. The tray 320b therefore supports the closed, filled dish P in the column 104b and the other dishes P' which may already be in the column 104b.

Next, in FIG. 9F the shuttle 31 is translated to its first stop position corresponding to FIG. 9B. In FIG. 9F the second openings 312b and 311b of the shuttle 31 lie underneath the first openings 115a and 104a, whilst the first openings 311a and 312a lie underneath the solid part 117 of the plate 11. During this translational movement, the rod 321a of the first piston 32a therefore passes from the second openings 311b and 312b to the first openings 311a and 312a and passes through the passages 311c and 312c arranged in the plates 311 and 312.

Figure 9G:
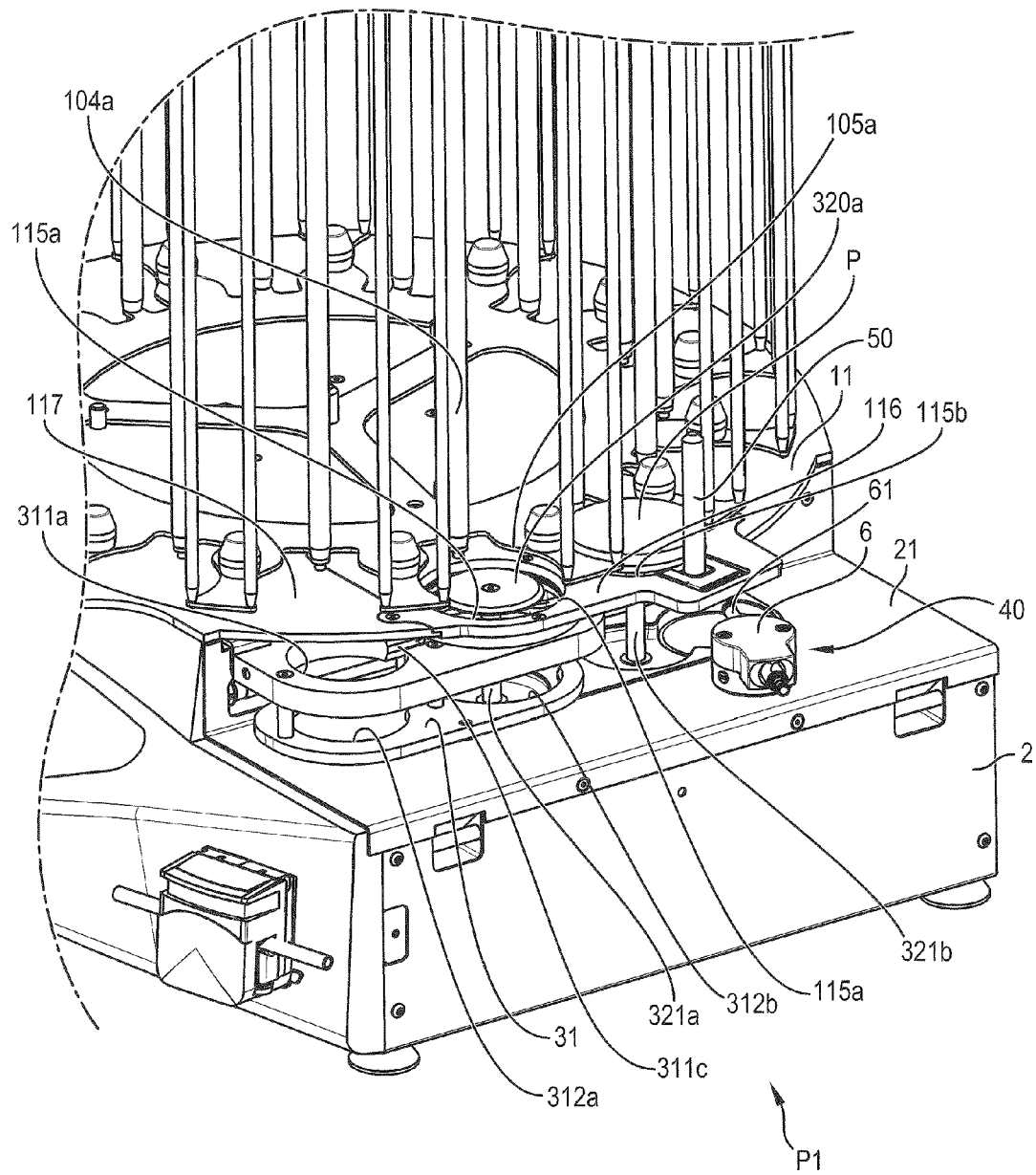

In FIG. 9G the trays 320a and 320b of the pistons then return to a lower position than the elevation position in FIG. 9F, this position in FIG. 9G corresponding to the position in FIGS. 9A and 10D. In FIGS. 9A and 9G, the Petri dishes in the column 104b are supported by means 106. Means 50 for vertical guiding of the dishes P, P' in the second column 104b are secured to the plate 11 in the vicinity of the opening 115b, and comprise for example a vertical bar 50 to cause the dishes P, P' to be stacked straight during the raising and lowering of the second piston 32b in FIGS. 10A to 10D.

The space taken up by the shuttle 31 is about that of two adjacent Petri dishes, corresponding to its position underneath two adjacent columns 104 as in FIG. 9C. The travel distance of the shuttle 31 in the illustrated embodiment corresponds to the distance between the two columns 104a and 104b of adjacent Petri dishes. The width of the first upper opening 311a is smaller than the width of the bottom part F of a Petri dish P to support the stack of Petri dishes originating from the first column 104a when this first upper opening 311a lies underneath as in FIGS. 9C and 9D.

Evidently, the shuttle 31 could have any shape other than the shape shown in the figures, whilst having a first vertical passageway 314a extending from the first lower opening 312a to the first upper opening 311a to allow movement of the first tray 320a of the first piston 32a therein, a second vertical passageway 314b extending from the second lower opening 312b to the second upper opening 311b for passing of the first and second trays 320a and 320b of the first and second pistons 32a and 32b, the third upper passageway 311c between the upper openings 311b and 311a and the fourth lower passageway 312c between the lower openings 312a and 312b, these third and fourth passageways 311c and 311d evidently possibly being only one passageway.

Owing to the small volume taken up by the shuttle 31, it is possible to form a carousel 10 having a larger number of columns 104. Therefore, for an equal number of Petri dishes P, it is possible to have a carousel 10 that is less tall since the Petri dishes are distributed over a larger number of columns 104. The manufacture of the device is also simpler and cheaper.

For optimal use of the device, the user fills all the columns 104 of the carousel except one with empty Petri dishes. The column that is empty of Petri dishes is brought by rotation of the carousel 10 to above the second opening 115b and above the tray 320b of the second piston 32b in FIG. 9A. The Petri dishes P derived from column 104a are then successively filled following the above-described method.

The filled dishes P are then transferred one by one into the column 104b which initially did not contain any dish. When the column 104a located above the first opening 115a no longer contains any dishes P, the carousel 10 is rotated in direction S illustrated in FIG. 1 to cause this new empty column to move to above the second opening 115b. This direction of travel S of the carousel by one column takes place in the same direction as from the first stop position P1 to the second stop position P2. In this case, a new column of empty Petri dishes, which was initially located on the solid part 112 of the plate 11, comes to lie above the first opening 115a for unstacking. The same process is then repeated with this stack of dishes.

The shuttle 31 also comprises a longitudinal end-passageway for the piston rod 321b i.e. in the illustrated embodiment, a first upper longitudinal end-passageway 311d in the top plate 311, wherein the passageway 311d opens firstly into the second upper opening 311b and secondly into the outside in the longitudinal direction, and a lower longitudinal end-passageway 312d in the bottom plate 312, placing the second lower opening 312b in communication with the outside in the longitudinal direction. For example, in FIG. 8 the second lower opening 312b and the passageway 312d are in the form of a notch in the bottom-plate 312, which opens towards the lower longitudinal end and towards one side 312e.

A detector may be provided to detect the presence of bottom part F in the second lower 312b opening. This detector is fixed for example relative to the base 2, to detect the presence of a bottom part F in the second lower opening 312b at the first stop position and/or at the second stop position. Provision may therefore be made for a first detector under the first column 104*a*. Provision may also be made for another detector under the second column 104*b*. The filling process of the dishes P is carried out for as long as the detector supplies information on the presence of a dish bottom part F in the opening 312*b*. If the detector does not supply such information on the presence of a dish bottom part F in the opening 312*b*, the process is interrupted or the feeding of product to the dispensing means 6 is interrupted.

The control and coordination means to control the different means for driving the carousel 10, pistons 32*a*, 32*b*, head 6 and shuttle 31 are automated and actuated by the control interface 5. For example, they are provided in the form of a microprocessor in the base 2. The device of the invention is intended to be integrated in an automated Petri dish filling machine.

According to one embodiment, the device comprises:

at least first and second columns (104*a*, 104*b*) for the vertical guiding of Petri dishes (P), respectively capable of receiving first and second stacks of Petri dishes with the lid placed over the bottom part, and capable of being respectively positioned above a first lower passageway (115*a*) for passing Petri dishes and above a second lower passageway (115*b*) for passing Petri dishes, the first and second passageways (115*a*, 115*b*) being provided on a fixed part (3) relative to the base (2), a system (30) for moving at least one Petri dish from the first column (104*a*) to the second column (104*b*), comprising:

a transfer member (31) having an upper opening (311*b*) supporting the lid (C) of a Petri dish above a second lower opening (312*b*) supporting the bottom part (F) of a Petri dish, dispensing means (6) for dispensing said product above the lower opening (312*b*) into the bottom part (F) of the Petri dish under the upper opening (311*b*), the mobile transfer member (31) being capable of taking up a first stop position, in which the supporting openings (311*b*, 312*b*) are located under the first passageway (115*a*), and a second stop position in which the supporting openings (311*b*, 312*b*) lie under the second passageway (115*b*), a first piston (32*a*) comprising a first tray (320*a*) located under the first passageway (115*a*) and capable of passing through the openings (311*b*, 312*b*) to lower the lid and bottom part of a Petri dish in the first column (104*a*) onto their respective supporting opening (311*b*, 312*b*) when the transfer member (31) lies in the associated first stop position, a second piston (32*b*) comprising a second tray (320*b*) located under the second lower passageway (115*b*) and capable of passing through the openings (311*b*, 312*b*) to lift the lid and the bottom of the Petri dish from their respective supporting opening (311*b*, 312*b*) into the second column (104*b*), when the transfer member (31) lies in the associated second stop position, the transfer member (31) being a shuttle (31) having translational movement relative to the base (2) with direct back and forth movement of the supporting openings (311*b*, 312*b*) between each of the first and second stop positions (P1, P2), the dispensing means (6) being arranged to dispense said product above the lower opening (312*b*) and under the upper opening (311*b*) into the bottom part (F) of the dish (P) when these openings (311*b*, 312*b*) lie in a selected one of the first and second stop positions (P1, P2).

According to one embodiment, the device comprises means for the synchronous driving of the pistons (32*a*, 32*b*) at the same height. According to one embodiment, the pistons (32*a*, 32*b*) are driven by the same motor. According to one embodiment, the device comprises means for coordinating the translational movements of the shuttle (31) and pistons (32*a*, 32*b*) so as to place them successively in the following positions:

the first stop position (P1) with a lowered position of the first tray (320*a*) under the lower opening (312*b*), to bring the lid of the dish onto the upper opening (311*b*) and to bring the bottom part of the dish onto the lower opening (312*b*), the second stop position (P2), with the first tray (320*a*) under the lower opening (312*b*) to dispense product into the bottom part (F) of the open dish located in the lower opening (312*b*), via the dispensing means (6), in the second stop position (P2), an elevation position of the second tray (320*b*) in the second column (104*b*) to close the lid over the bottom part of the dish and to transfer this closed dish into the second column, the first stop position (P1), with a lowered position of the first tray (320*a*) under the lower opening (312*b*).

According to one embodiment, the dispensing means (6) comprise an outlet nozzle (61) for outputting said product, means for moving the dispensing nozzle (6) being provided to cause it to move between either one of a dispensing position of said product in which the nozzle (6) lies above the lower opening (312*b*) and under the upper opening (311*b*) in said selected stop position, and a retracted position in which the nozzle (6) no longer lies between the openings (311*b*, 312*b*), control means being provided so as only to allow movement of the piston (32*a*, 32*b*) associated with the selected stop position when the nozzle (6) is in the retracted position. According to one embodiment the shuttle (31), in addition to said upper and lower supporting openings (311*b*, 312*b*) called second openings (311*b*, 312*b*), also comprises means (311*b*) for supporting the bottom part (F) of Petri dishes provided with a first opening (311*b*) allowing the passing of the first piston (32*a*) in the first stop position.

According to one embodiment the shuttle (31), in addition to said upper and lower supporting openings (311*b*, 312*b*) called second openings 311*b*, 312*b*, and to the first upper and lower openings (311*a*, 312*a*), the shuttle 31 comprises a bottom plate 312 and a top plate 311 spaced from each other by a prescribed distance to form a passageway for the dispensing means (6) in the dispensing position, the bottom plate (312) comprising the first lower opening (312*a*) for passing of the first tray (320*a*) and first piston (32*a*) and said second lower opening (312*b*) for supporting the bottom part of the dish, the top plate (311) comprising a first upper opening (311*a*) for passing of the first tray (320*a*) and first piston (32*a*), and said second upper opening (311*b*) for supporting the lid, the first upper opening (311*a*) lying above the first lower opening (312*a*). According to one embodiment, the device comprises means for lifting the first tray (320*a*) of the first piston (32*a*) above the shuttle (31), the first tray (320*a*) is fixed to at least one lower rod (321*a*) connecting the first tray (320*a*) to said lifting means, the shuttle (31) comprises at least one passageway (311*c*, 312*c*) to place the second openings (311*b*, 312*b*) in communication with the first opening (311*a*) or first openings (311*a*, 312*a*) to allow the passing of said lower supporting rod (321*a*) as the shuttle (31) moves between the stop positions (P1, P2) when the first tray (320*a*) is in raised position above the shuttle (31). According to one embodiment, the device comprises at least one carousel (10) mounted in rotation on a vertical shaft of the base (2), the carousel comprising a plurality of columns (104*a*, 104*b*) for vertical guiding of the Petri dishes (P), each capable of receiving a stack of Petri dishes with the lid placed over the bottom part, means for driving the carousel (10) in rotation being provided to bring two of the columns (104a, 104b) respectively above the first lower Petri dish passageway (115a) and above the second lower passageway (115b) to form said first and second columns (104a, 104b).

According to one embodiment, the device comprises means (106) for retaining and for passing Petri dishes (P, P') above the second passageway (115b), these retaining and passing means (106) being mobile between a first retaining position for retaining the Petri dishes (P, P') above the second passageway (115b) in the second column (104b), and a second position for the released passing of the Petri dishes in the second passageway (115b), constraining means for constraining to the first retaining position being provided, means being provided to lift the second tray (320b) of the second piston (32b) as far as a prescribed elevation position in the second column (104b), the retaining means (106) being arranged so that they can be actuated in the second released passing position by abutment against said lid of the Petri dish when the second tray (320b) of the second piston (32b) carrying the dish with this lid is lifted as far as the prescribed elevation position in the second column (104b), the retaining means (106), in the first retaining position, providing a passage width that is narrower than the width of the bottom part of the Petri dish to bring support thereto, and wider than the width of the second tray (320b) of the second piston (32b) to allow lowering thereof underneath the second column (104b).

The invention claimed is:

1. A device for dispensing a prescribed product into at least one Petri dish, each Petri dish comprising a removable lid able to be placed over a bottom part of smaller width, the device comprising:
  a transfer member operably transferring the Petri dish to a product dispensing station where the Petri dish is held with a space between its lid and bottom part to allow the dispensing of product via a product dispensing head comprising an outlet nozzle dispensing product into the bottom part when the outlet nozzle is in a product dispensing position
  a piston comprising a determined tray supporting the bottom part at the product dispensing station;
  a driver operably rotating the determined tray around itself relative to the product dispensing head arranged to cause the bottom part to rotate relative to the product dispensing head lying in the product dispensing position into the bottom part, wherein the outlet nozzle is arranged relative to the determined tray to dispense product into the bottom part set in rotation;
  the transfer member transferring the bottom part as far as a determined stop position at the product dispensing station, the transfer member having an upper supporting opening for supporting the lid of the Petri dish above a lower supporting opening for supporting the bottom part of the Petri dish, the determined tray being capable of passing through the openings to lift the bottom part of the Petri dish into the lid by passing through their respective supporting opening when the transfer member lies in the determined stop position at the product dispensing station; and
  the piston provided with the determined tray having the function of rotating the bottom part of the Petri dish during the dispensing of product into the bottom part in the product dispensing position, and having the function of lifting the bottom part of the Petri dish through the upper supporting opening to insert the bottom part into the lid of the Petri dish in the determined stop position.

2. The dispensing device according to claim 1, further comprising a speed of rotation of the determined tray around itself is between 10 and 100 rotations per minute.

3. The device according to claim 1, wherein the driver operably driving in rotation is provided to cause the determined tray to rotate around itself about a geometric axis of rotation, and the outlet nozzle comprises a product outlet end located away from the geometric axis of rotation of the determined tray set in rotation around itself in the product dispensing position.

4. The device according to claim 1, wherein the driver operably driving in rotation is designed to cause the determined tray to rotate around itself about a geometric axis of rotation, and the outlet nozzle is arranged to dispense product into a region of the bottom part, this region lying at a distance from the geometric axis of rotation of the determined tray set in rotation in the product dispensing position.

5. The device according to claim 1 wherein the determined tray comprises an upper surface that is concave from its center towards its periphery to receive the bottom part of the Petri dish.

6. The device according to claim 5, wherein the upper surface of the determined tray comprises a peripheral contacting part for contacting with the bottom part of the Petri dish.

7. The device according to claim 5, wherein the determined tray carries a recess in its center on its upper surface.

8. The device according to claim 1, wherein the upper surface of the determined tray comprises a first peripheral contacting part for contacting with the bottom part of the Petri dish, wherein this first peripheral contacting part is in a material having greater adherence than the material of a second part of the upper surface of the determined tray, surrounded by this first peripheral contacting part.

9. The device according to claim 8, wherein the first peripheral contacting part is in rubber material, whereas the second part surrounded by this first peripheral contacting part is metallic.

10. A device comprising:
  (a) at least first and second columns for the vertical guiding of Petri dishes, capable of receiving first and second stacks of the Petri dishes respectively with a lid placed over a bottom part of each petri dish and capable of being respectively positioned above a first passageway for passage of the Petri dishes and above a second passageway for passage of the Petri dishes, the first and second passageways being provided on a fixed part relative to a base;
  (b) a system operably for moving at least one of the Petri dishes from the first column to the second column comprising:
    a transfer member being mobile and capable of taking up a first stop position in which supporting openings of the transfer member lie under the first passageway, and a second determined stop position at the product dispensing station in which the supporting openings lie under the second passageway;
    a product dispensing head arranged to dispense product above a lower supporting opening into the bottom part of the Petri dish under the upper supporting opening in the second determined stop position;
    a first piston comprising a first tray located under the first passageway and capable of passing through the supporting openings to lower the lid and the bottom part of a Petri dish of the first column onto their respective supporting opening when the transfer member lies in the associated first stop position; and a second piston comprising a second determined tray located under the second lower passageway and capable of passing through the supporting openings to lift the lid and the bottom part of the Petri dish from their respective supporting opening into the second column when the transfer member lies in the associated second stop position;

(c) the transfer member being a shuttle with translational movement relative to the base in direct back and forth movement of the supporting openings between each of the first and second stop positions.

11. The device according to claim 10, wherein one of the columns for the vertical guiding of the Petri dishes is arranged above the second piston to receive at least one of the Petri dishes having its bottom part lifted into its lid via the second piston at the product dispensing station, the second piston being arranged to move the Petri dish with its bottom part lifted into its lid from the transfer member to the column for vertical guiding of the Petri dishes, the column for vertical guiding of the Petri dishes comprising a retainer operably retaining the Petri dish having its bottom part lifted into its lid which has been brought by the second piston.

12. A method for dispensing a prescribed product into at least one Petri dish using a dispensing device, each Petri dish comprising a removable lid able to be placed over a bottom part of smaller width, the method comprising:

opening the Petri dish to hold its lid away from its bottom part;

bringing the bottom part to a product dispensing station;

placing a dispensing head in a product dispensing position to dispense product into the bottom part located at the dispensing station;

positioning the bottom part of the Petri dish on a piston comprising a determined tray rotating around itself, to cause the bottom part to rotate around itself throughout the entire time that product is dispensed into the bottom part by the product dispensing head in product dispensing position at the product dispensing station;

bringing the bottom part as far as a determined stop position at the product dispensing station by a transfer member having an upper supporting opening for supporting the lid of the Petri dish above a lower supporting opening for supporting the bottom part of the Petri dish, the determined tray being capable of passing through the supporting openings to lift the bottom of the Petri dish into the lid by passing through their respective supporting opening, when the transfer member lies in the determined stop position at the product dispensing station;

wherein the piston provided with the determined tray rotates the bottom part of the Petri dish while product is dispensed into the bottom part in the product dispensing position, then lifts the bottom part of the Petri dish through the upper supporting opening to insert the bottom part into the lid of the Petri dish in the determined stop position at the product dispensing station.

* * * * *